United States Patent [19]

Nakane et al.

[11] Patent Number: 4,663,336

[45] Date of Patent: May 5, 1987

[54] 7-OXABICYCLOHEPTANE SUBSTITUTED DIAMIDE AND ITS CONGENER PROSTAGLANDIN ANALOGS USEFUL IN THE TREATMENT OF THROMBOTIC DISEASE

[75] Inventors: Masami Nakane, Aichi, Japan; Joyce Reid, Dayton, N.J.

[73] Assignee: E. R. Squibb & Sons, Inc., Princeton, N.J.

[21] Appl. No.: 853,788

[22] Filed: Apr. 18, 1986

Related U.S. Application Data

[63] Continuation-in-part of Ser. No. 750,948, Jul. 1, 1985, abandoned.

[51] Int. Cl.$^4$ .................. A61K 31/34; A61K 31/357; G07D 307/00
[52] U.S. Cl. .................... 514/381; 514/469; 549/463
[58] Field of Search ........... 548/253; 549/463; 514/381, 469

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,617 | 6/1984 | Nakane et al. | 424/285 |

FOREIGN PATENT DOCUMENTS

| | | |
|---|---|---|
| 0043292 | 8/1982 | European Pat. Off. |
| 0082646 | 6/1983 | European Pat. Off. |
| 2039909 | 8/1980 | United Kingdom |

Primary Examiner—John M. Ford
Assistant Examiner—Bernard I. Dentz
Attorney, Agent, or Firm—Lawrence S. Levinson; Burton Rodney

[57] ABSTRACT

7-Oxabicycloheptane substituted amide prostaglandin analogs are provided having the structural formula

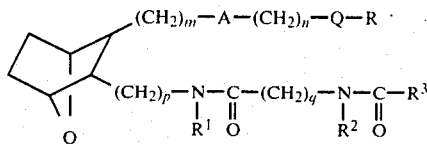

wherein m is 0 to 4; A is —CH=CH— or —CH$_2$—CH$_2$—; n is 1 to 5; Q is —CH=CH—, —CH$_2$—,

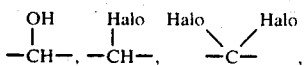

or a single bond; R is CO$_2$H, CO$_2$alkyl, CO$_2$alkali metal, CO$_2$polyhydroxyamine salt, —CH$_2$OH,

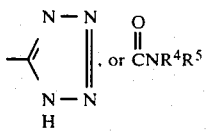

wherein R$^4$ and R$^5$ are the same or different and are H, lower alkyl, hydroxy, lower alkoxy or aryl, at least one of R$^4$ and R$^5$ being other than hydroxy and lower alkoxy; p is 1 to 4; R$^1$ is H or lower alkyl; q is 1 to 12; R$^2$ is H or lower alkyl; and R$^3$ is H, lower alkyl, lower alkenyl, lower alkynyl, aryl, arylalkyl, lower alkoxy, aryloxy, arylalkyloxy, amino, alkylamino arylamino, arylalkylamino,

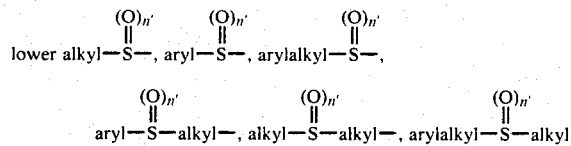

(wherein n' is 0, 1 or 2), alkylaminoalkyl, arylaminoalkyl, arylalkylaminoalkyl, alkoxyalkyl, aryloxyalkyl or arylalkoxyalkyl.

The compounds are cardiovascular agents useful, for example, in the treatment of thrombotic disease.

33 Claims, No Drawings

7-OXABICYCLOHEPTANE SUBSTITUTED DIAMIDE AND ITS CONGENER PROSTAGLANDIN ANALOGS USEFUL IN THE TREATMENT OF THROMBOTIC DISEASE

REFERENCE TO OTHER APPLICATIONS

This application is a continuation-in-part of U.S. application Ser. No. 750,948, filed July 1, 1985 now abandoned.

DESCRIPTION OF THE INVENTION

The present invention relates to 7-oxabicycloheptane substituted diamide and congener prostaglandin analogs which are cardiovascular agents useful, for example, in the treatment of thrombotic disease. These compounds have the structural formula

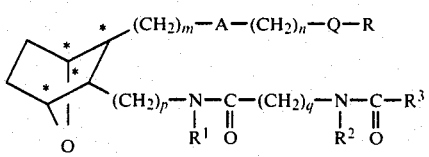

including all stereoisomers thereof, wherein m is 0 to 4; A is —CH=CH— or —CH$_2$—CH$_2$—; n is 1 to 5; Q is —CH=CH—, —CH$_2$—,

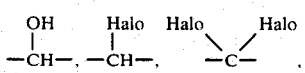

or a single bond; R is CO$_2$H, CO$_2$alkyl, CO$_2$ alkali metal, CO$_2$polyhydroxyamine salt, —CH$_2$OH,

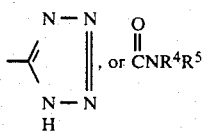

wherein R$^4$ and R$^5$ are the same or different and are H, lower alkyl, hydroxy, lower alkoxy or aryl at least one of R$^4$ and R$^5$ being other than hydroxy and lower alkoxy; p is 1 to 4; R$^1$ is H or lower alkyl; q is 1 to 12; R$^2$ is H or lower alkyl; and R$^3$ is H, lower alkyl, lower alkenyl, lower alkynyl, aryl, arylalkyl, lower alkoxy, arylalkyloxy, aryloxy, amino, alkylamino, arylalkylamino, arylamino,

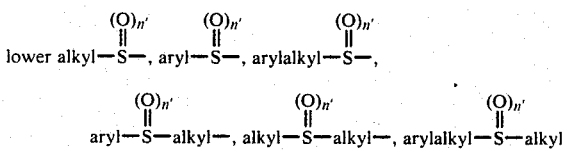

(wherein n' is 0, 1 or 2), alkylaminoalkyl, arylaminoalkyl, arylalkylaminoalkyl, alkoxyalkyl, aryloxyalkyl or arylalkoxyalkyl.

The term "lower alkyl" or "alkyl" as employed herein alone or as part of another group includes both straight and branched chain hydrocarbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkylaryl substituent, a haloaryl substituent, a cycloalkyl substituent, an alkylcycloalkyl substituent, hydroxy, an alkylamido substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino grops, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3- nonynyl, 4-decynyl, 3-undecynyl, 4-dodecynyl and the like.

The terms $(CH_2)_m$, $(CH_2)_n$ and $(CH_2)_p$ includes straight or branched chain radicals having from 0 to 4 carbons in the normal chain in the case of $(CH_2)_m$, from 1 to 5 carbons in the normal chain in the case of $(CH_2)_n$ and from 1 to 4 carbons in the normal chain in the case of $(CH_2)_p$ and may contain one or more lower alkyl and/or halogen substituents. Examples of $(CH_2)_m$, $(CH_2)_n$ and $(CH_2)_p$ groups include $CH_2$,

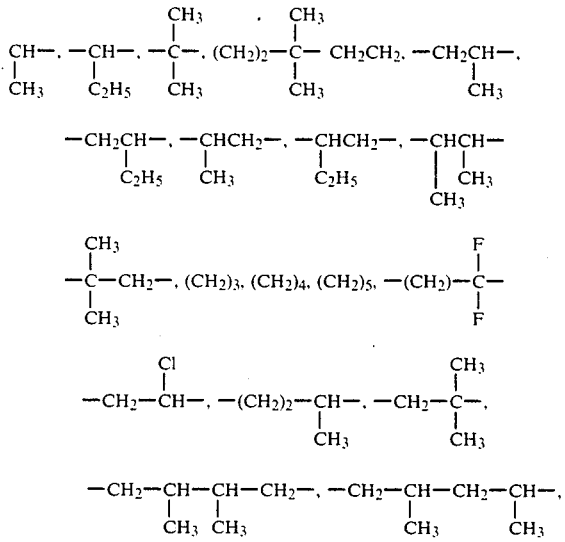

and the like.

The term $(CH_2)_q$ includes straight or branched chain radicals having from 1 to 12 carbons in the normal chain and includes any of the above examples of $(CH_2)_m$, $(CH_2)_n$ and $(CH_2)_p$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, amide, thioamide, thiol, alkylthio, arylthio, cyano or nitro groups.

The term "amide" refers to the group

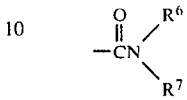

wherein $R^6$ and $R^7$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I wherein m is 1 or 2, A is a $-CH=CH-$, n is 1 or 4, Q is a single bond or $-C(F_2)-$,

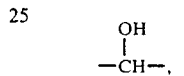

$(CH_2)_2$, or $-CH=CH$, R is $CO_2H$ or $CH_2OH$; p is 1, $R^1$ is H, $(CH_2)_q$ is $-CH_2-$; $R^2$ is H or $CH_3$, and $R^3$ is lower alkyl, such as pentyl, hexyl, or heptyl or lower alkoxy, such as pentoxy, lower alkylamino such as pentylamino or arylthioalkyl, such as phenylthiomethyl.

The compounds of formula I of the invention may be prepared as described below.

A. p is 1, m is 1, Q is $-CH_2-$ or a single bond and $R^1$ is H

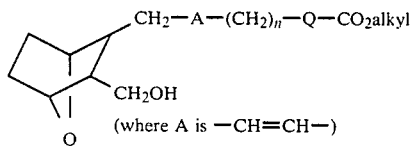

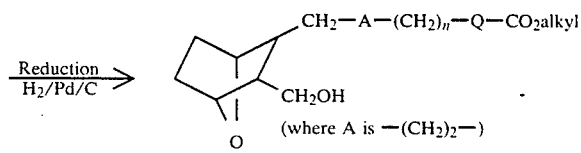

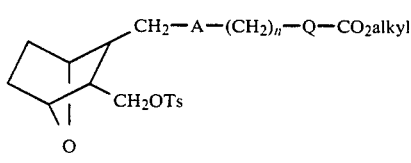

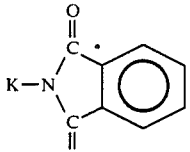

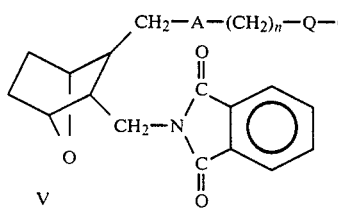

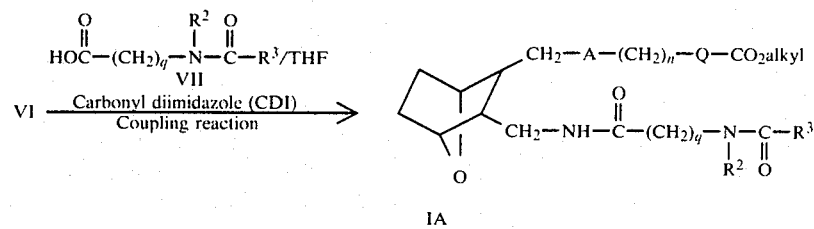
A'. Where p is 1, m is 1, Q is —CH₂— or a single bond and R¹ is alkyl
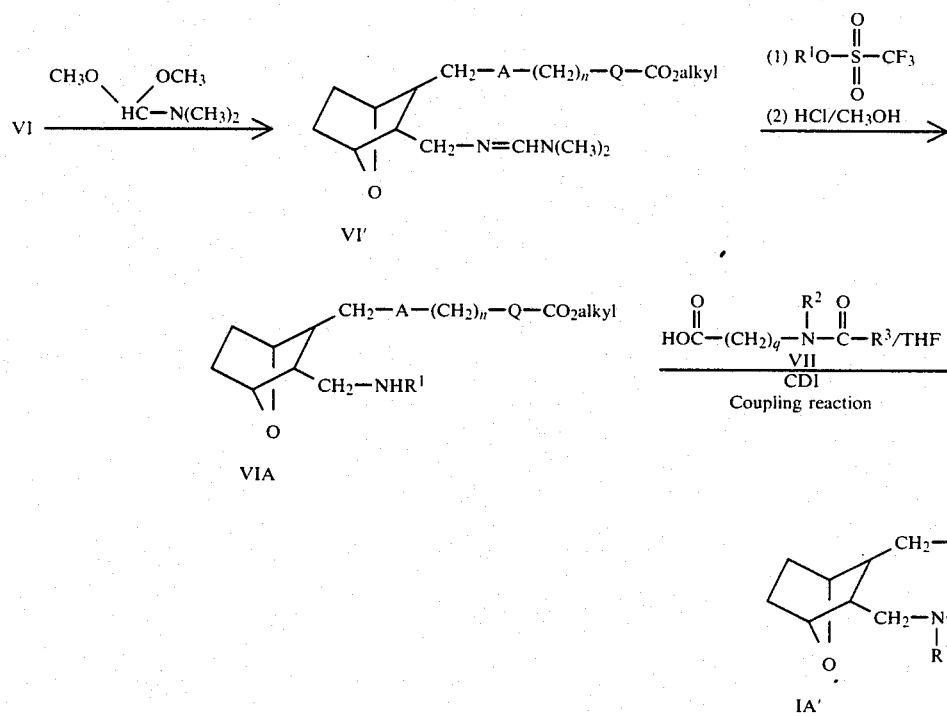
B. Where Q is CH₂ or a single bond, p is 2 to 5, m is 1 and R¹ is H
II
or   $\xrightarrow{\text{Collins oxidation}}$
IIA
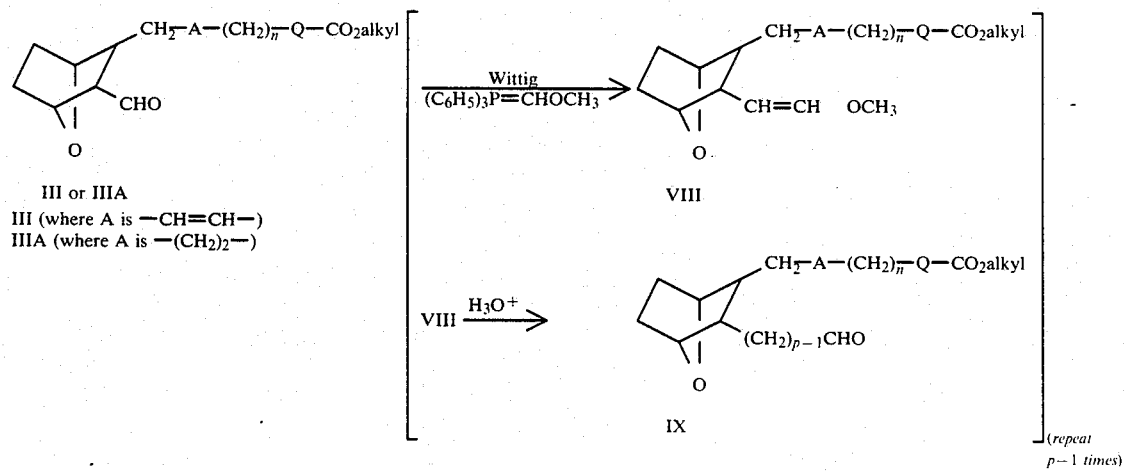

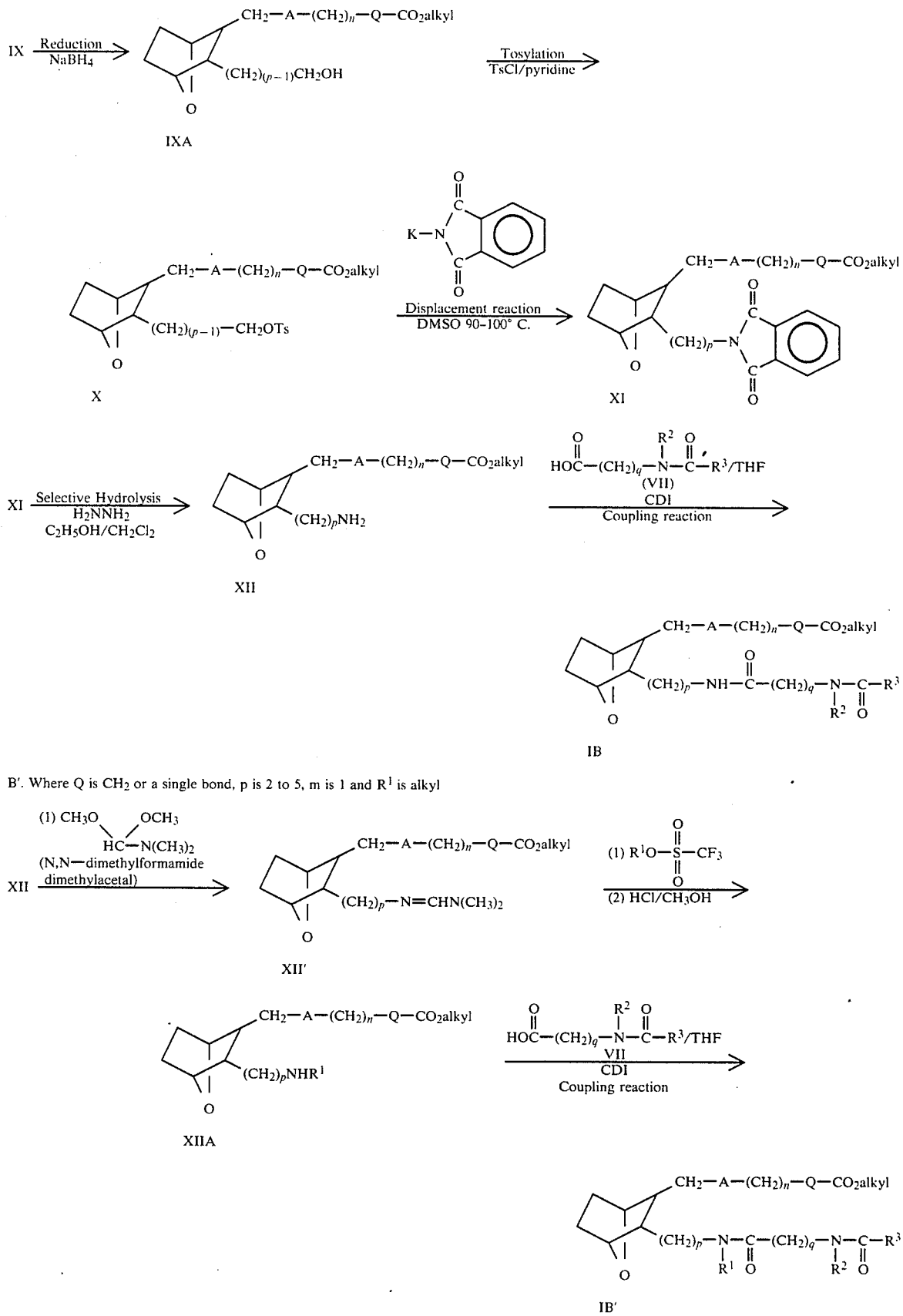
B′. Where Q is CH₂ or a single bond, p is 2 to 5, m is 1 and R¹ is alkyl
C. Where m is 2, p is 1, A is —CH=CH— and Q is CH₂ or a single bond -continued
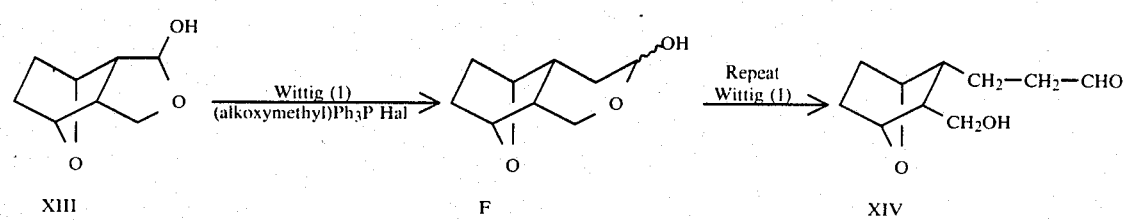
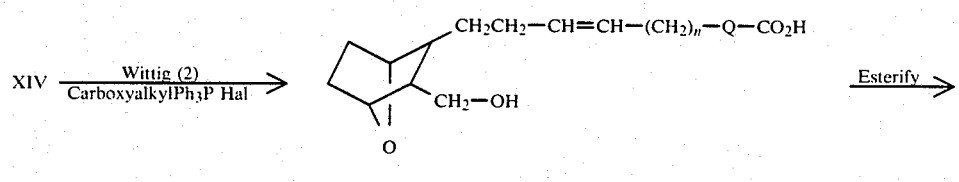
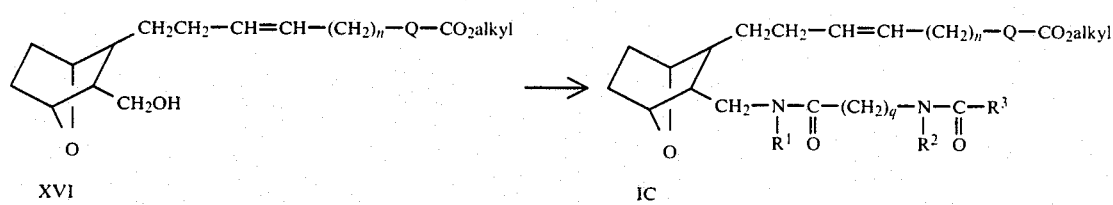
D. m is 2, p is 1, A is —CH₂—CH₂— and Q is CH₂ or a single bond
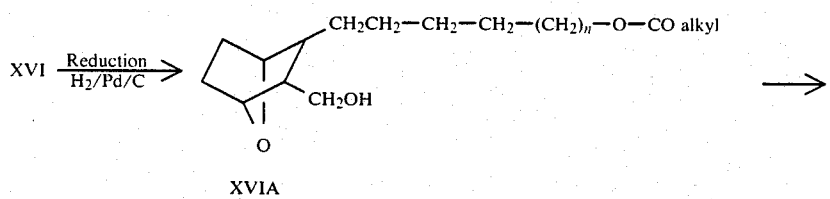
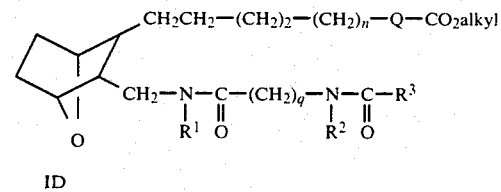
E. Where m is 3 or 4, p is 1, A is —CH=CH— and Q is CH₂ or a single bond
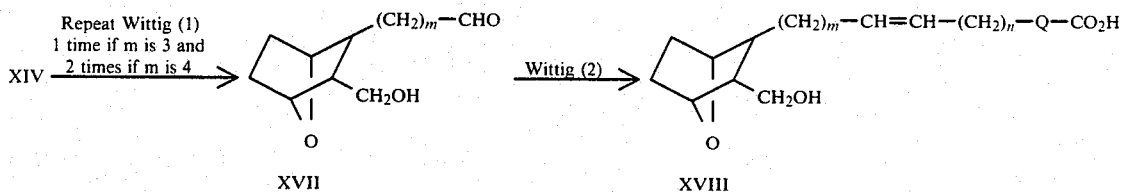
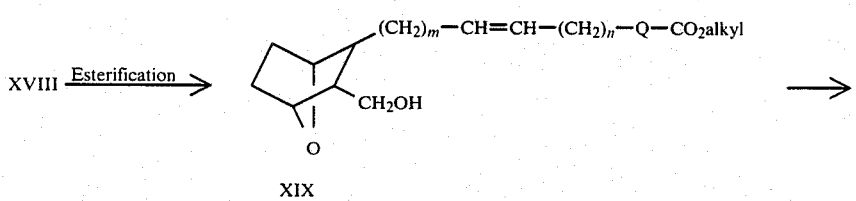

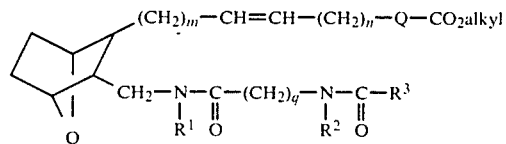
IE
F. Where m is 3 or 4, p is 1, A is CH₂CH₂ and Q is CH₂ or a single bond
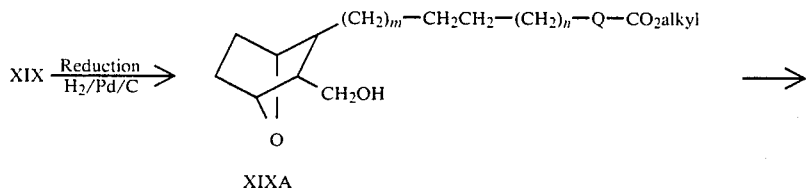
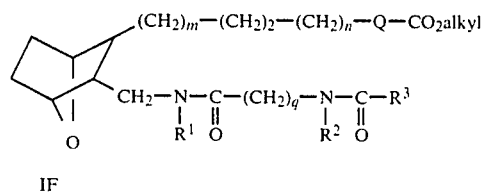
IF
G. Where m = 0, A is —CH=CH—, p is 1, Q is CH₂ or a single bond
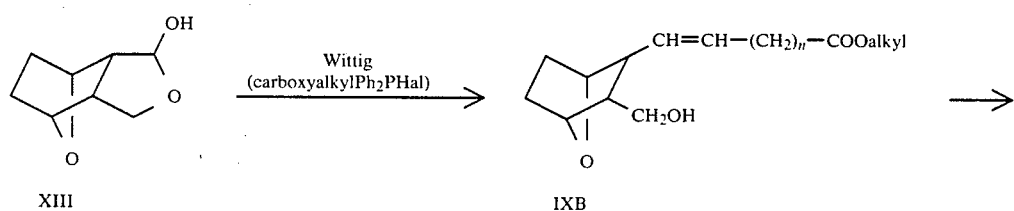
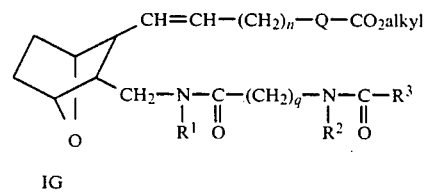
IG
H. Where m = 0, A is —(CH₂)₂—, p is 1, Q is CH₂ or a single bond
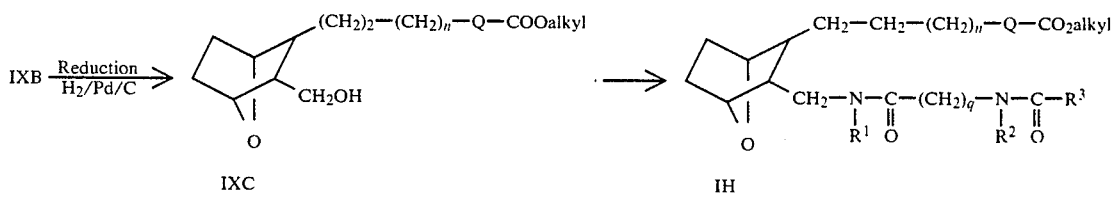
I. Where Q is —CH=CH—
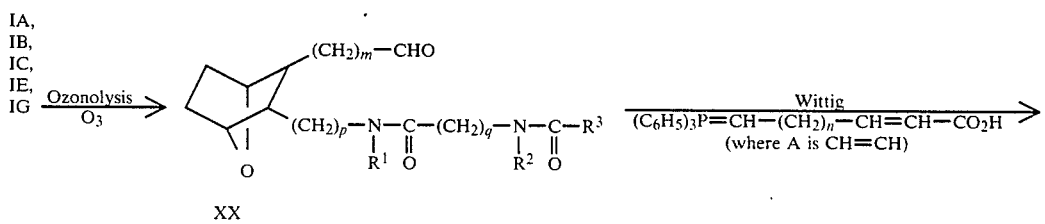

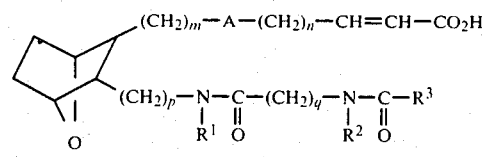

IJ

J. Where Q is 
$$-\overset{halo}{\underset{|}{CH}}- \quad \text{or} \quad -\overset{halo}{\underset{|}{\underset{halo}{C}}}-$$

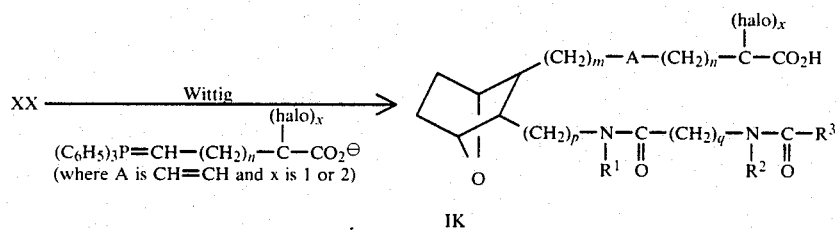

IK

K. Where Q is $-\overset{OH}{\underset{|}{CH}}-$

IA,
IB,
IC,
ID,
IE,
IF,
IG,
IH (1) LiN(i-C$_3$H$_7$)$_2$
(2) MoO$_5$PyHMPA

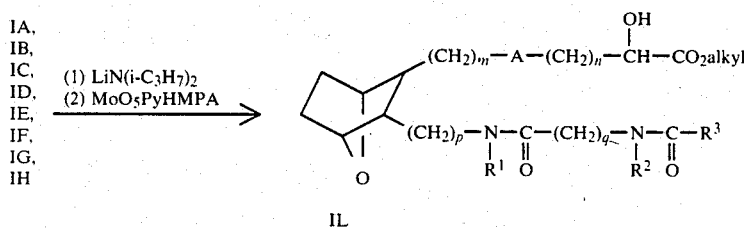

IL

L. Where R is $\overset{O}{\underset{\|}{C}}NR^1R^5$ (wherein $R^4$ and $R^5$ are other than hydroxy or alkoxy)

IA,
IB,
IC,
ID,
IE,
IF,
IG,
IH,
or IL
or esters of
IJ or IK

HNR$^4$R$^5$ →

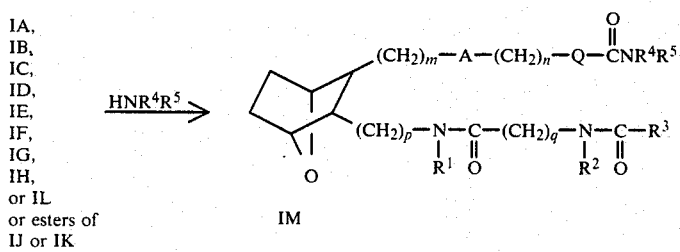

IM

M. Where R is $-\underset{\underset{H}{\overset{N-N}{\underset{\|}{N-N}}}}{}$ and A is CH=CH

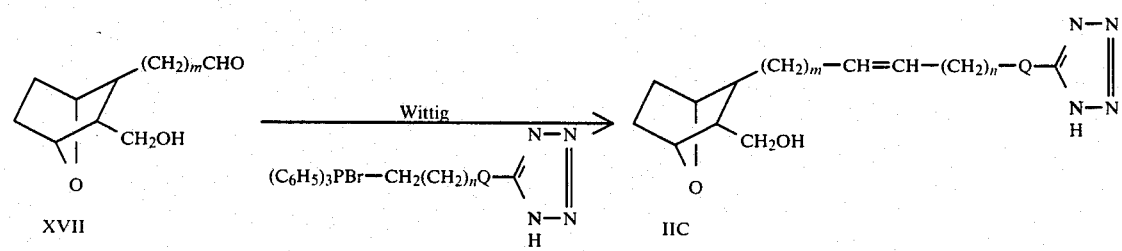

XVII → Wittig, (C$_6$H$_5$)$_3$PBr—CH$_2$(CH$_2$)$_n$Q— → IIC

IIC → 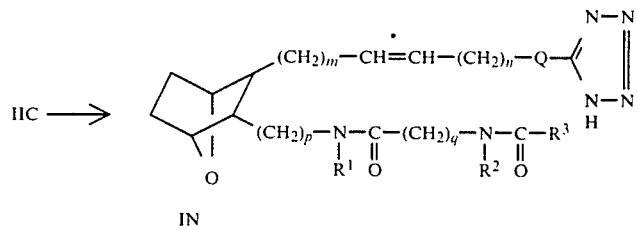

IN

N. Where R is 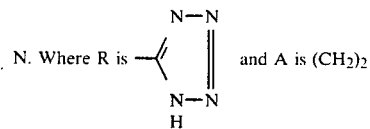 and A is $(CH_2)_2$

IN $\xrightarrow[H_2/Pd/C]{Reduction}$ 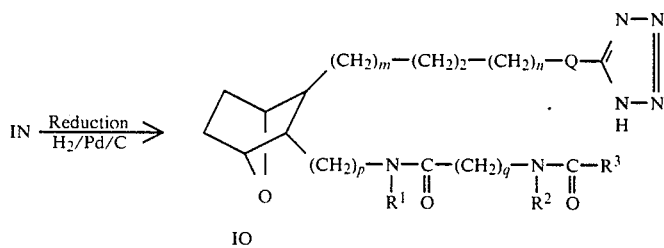

IO

O. Where R is $CH_2OH$

IA to IH, IL, or esters of IJ and IK $\xrightarrow[LiBH_4]{NaBH_4 \text{ or}}$ 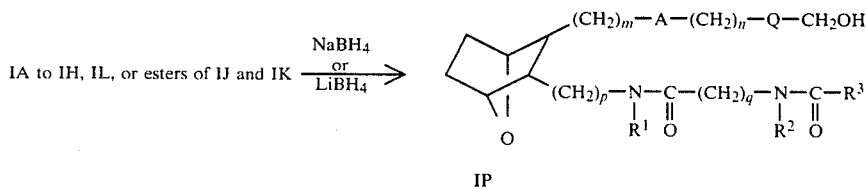

IP

P. Where R is $CO_2H$

IA to IH, IL $\xrightarrow{\text{Hydrolysis} \atop \text{LiOH, HCl}}$ 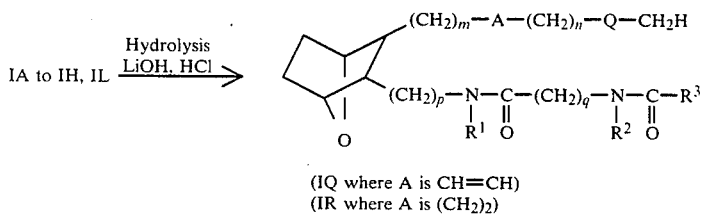

(IQ where A is CH=CH)
(IR where A is $(CH_2)_2$)

Q. Where R is 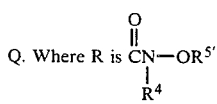

IQ or IR $\xrightarrow[\substack{(2)}]{\substack{\text{Hydroxamate Formation} \\ \text{(1) ClCOCOCl, benzene, } N_2, \text{ R.T.} \\ \text{cat. DMF}}}$ 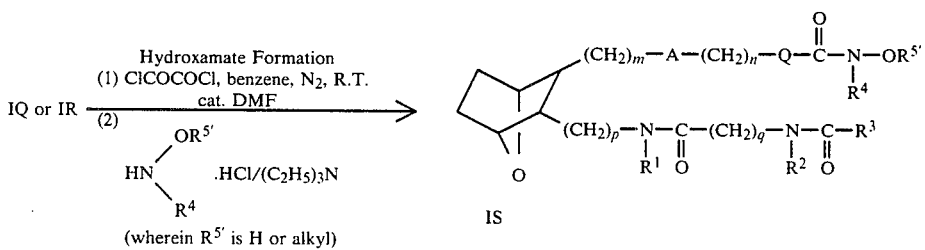

$\underset{R^4}{HN} \diagup \overset{OR^{5'}}{\phantom{X}} \cdot HCl/(C_2H_5)_3N$ (wherein $R^{5'}$ is H or alkyl)

IS

R. Where $R^3$ is $NH_2$

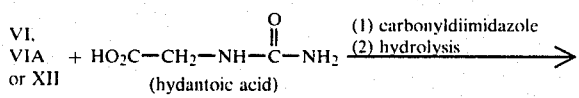
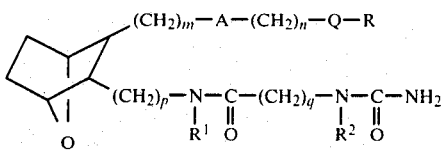

IT

As seen in reaction sequence "A", compounds of the invention where Q is —CH$_2$— or a single bond, p is 1, R is CO$_2$ alkyl, and R$^1$ is H, that is

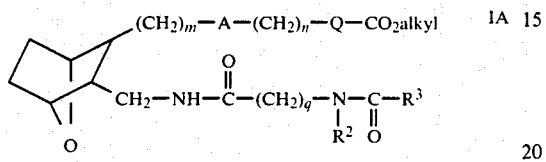 IA

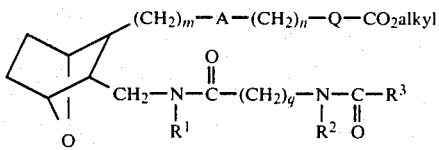

(IA—where R$^1$ is H
IA'—where R$^1$ is lower alkyl)

The reaction sequences identified as "B" and "B'" are employed to prepare compounds of the invention wherein Q is —CH$_2$— or a single bond, p is 2 to 5, and R is CO$_2$alkyl, that is, are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

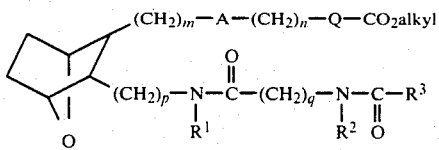

(where p is 2 to 5)

(IB—where R$^1$ is H
IB'—where R$^1$ is alkyl)

Compound II or IIA is used to form the aldehyde III (where A is —CH=CH—) or IIIA (where A is —(CH$_2$)$_2$). Thus, to form aldehyde III where A is —CH=CH—, compound II is subjected to a Collins oxidation, for example, by reacting II with chromium trioxide in pyridine. To form the aldehyde IIIA (where A is (CH$_2$)$_2$) compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IIIA (where A is (CH$_2$)$_2$). The aldehyde III or IIIA is used to prepare aldehyde IX (where p is 2-5) by carrying out a homologation sequence, such as a Wittig reaction with (C$_6$H$_5$)$_3$P=CHOMe followed by hydrolysis, (p−1) times. The aldehyde IX (where p is 2-5) is then carried on to compounds of this invention where p is 2-5, that is

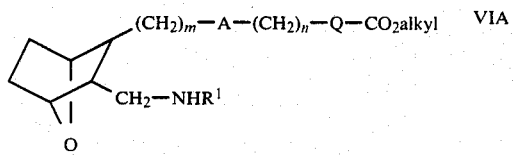 VI

As seen in reaction sequence "A'", where R$^1$ is lower alkyl, an alkylation reaction is carried out as in the reference M. J. O'Donnell et al., Tetrahedron Lett. (1984), 25, 3651-3654 to give VIA

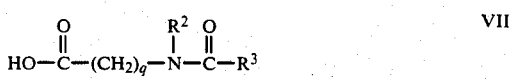 VIA

The amine VI or VIA is then subjected to a CDI coupling reaction by reacting VI or VIA with acid VII $$\underset{\text{VII}}{\text{HO}-\overset{O}{\overset{\|}{C}}-(CH_2)_q-\overset{R^2}{\underset{|}{N}}-\overset{O}{\overset{\|}{C}}-R^3}$$

in the presence of an inert organic solvent such as tetrahydrofuran and carbonyl diimidazole under an inert atmosphere, such as argon, employing a molar ratio of VI:VII of within the range of from about 1:1 to about 1:1.2, to form the amide ester compound of the invention IA or IA'

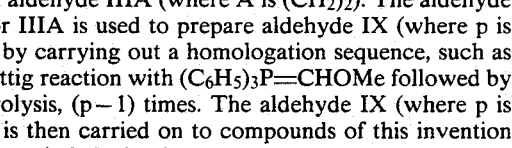

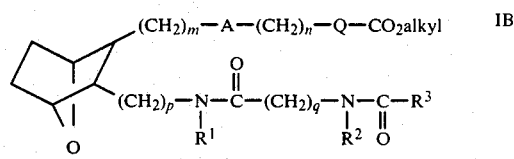 IB (where p is 2 to 5)
by reducing aldehyde IX by reacting with a reducing agent such as sodium borohydride to form alcohol IXA

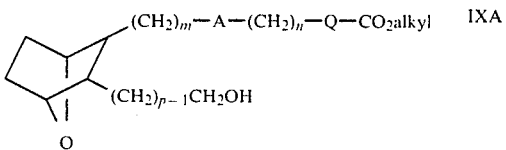

tosylating alcohol IXA as described above to form the tosylate X which is subjected to a displacement reaction with potassium phthalimide as described above to form the phthalimide XI. Phthalimide XI is then made to undergo selective hydrolysis as described above to form the amine XII

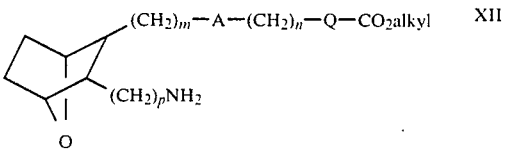

As seen in reaction sequence "B'", where $R^1$ is lower alkyl, an alkylation reaction is carried out as in O'Donnell et al, supra to give XIIA

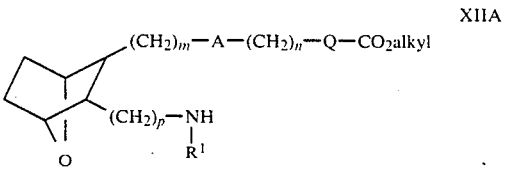

The amine XII or XIIA is then reacted with acid VII in a CDI coupling reaction as described above to form the amide ester compound of the invention IB or IB'

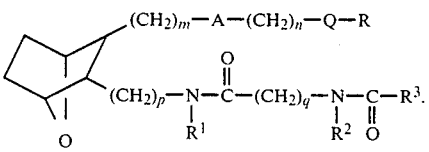

(IB—where $R^1$ is H
IB'—where $R^1$ is lower alkyl)

Compounds of the invention wherein m is 2, A is —CH=CH—, p is 1 and Q is $CH_2$ or a single bond may be prepared as outlined in reaction sequence "C" by subjecting starting compound XIII to a Wittig reaction, referred to as Wittig (1), by reacting XIII with an alkoxymethyltriphenyl phosphonium halide, such as (methoxymethyl)triphenylphosphonium chloride, for example, as described in Example 4 of U.S. Pat. No. 4,143,054, to form compound F. The Wittig (1) procedure is repeated on compound F to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is then employed in place of compound II in reaction scheme "A" to form compound IC of the invention.

As seen in reaction sequence "D", compounds of the invention wherein m is 2, A is —$CH_2$—$CH_2$—, p is 1 and Q is $CH_2$ or a single bond may be prepared as outlined in reaction sequence "D" by reducing hydroxymethyl compound XVI to form compound XVIA which is then employed in place of compound IIA in reaction sequence "A" to form compound ID of the invention.

Referring to reaction sequence "E", compounds of the invention wherein m is 3 or 4, A is —CH=CH—, p is 1 and Q is $CH_2$ or a single bond may be prepared by subjecting aldehyde XIV to the Wittig (1) procedure on time in the case where m is 3 and a second time in the case where m is 4, to form the aldehyde XVII. Aldehyde XVII is then subjected to the Wittig (2) procedure to form acid XVIII which is esterified to form ester XIX which is then employed in place of compound II in reaction scheme "A" to form compound IE of the invention.

As seen in reaction sequence "F", compounds of the invention wherein m is 3 or 4, A is $CH_2CH_2$, p is 1 and Q is $CH_2$ or a single bond may be prepared by reducing hydroxymethyl compound XIX to form compound XIXA which is then employed in place of compound II in reaction scheme "A" to form compound IF of the invention.

Thus, compounds of the invention wherein m is 0, 2, 3 or 4 and p is 2, 3 or 4 may be prepared by substituting hydroxymethyl compound XVI, XVIA, XIX, or XIXA in place of hydroxymethyl compound II or IIA in reaction sequences A and B.

Referring now to reaction sequence "G", compounds of the invention wherein m is 0, A is CH=CH, p is 1 and Q is $CH_2$ or a single bond, that is, compound IG may be prepared by subjecting compound XIII (prepared as described in Example 3 of U.S. Pat. No. 4,143,054) to a Wittig reaction, for example, as described in Example 6(c) of U.S. Pat. No. 4,143,054, by reacting B with a carboxyalkyltriphenyl phosphonium halide, such as carboxypentyltriphenyl phosphonium bromide to form the hydroxymethyl compound IXB which may then be used to form the ester IG which, in turn, may be hydrolyzed to the corresponding acid.

As seen in reaction sequence "H", where it is desired to prepare compounds of the invention wherein m is 0 and A is $(CH_2)_2$, the hydroxymethyl compound IXB is reduced by treatment with hydrogen in the presence of a palladium on carbon catalyst to form hydroxymethyl compound IXC which may then be used to form ester IH which then may be hydrolyzed to the corresponding acid.

Referring to reaction sequence "I", compounds of formula I of the invention wherein Q is —CH=CH—, that is IJ

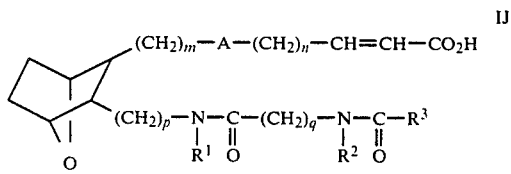

may be prepared by subjecting ester IA, IB, IA', IB', IC, IE and IG to ozonolysis by treating IA, IB, IA', IB', IC, IE and IG with ozone at −78° C. in methylene chloride and methanol to form aldehyde XX.

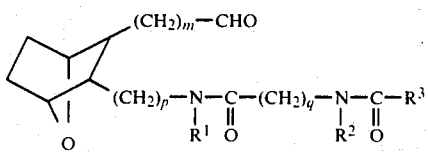

which is then treated with Wittig reagent

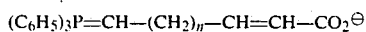

(where A is (—CH=CH—))
to form IJ.

In reaction sequence "J" compounds wherein Q is

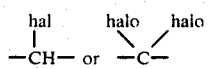

are prepared by subjecting aldehyde XX to a Wittig reaction with

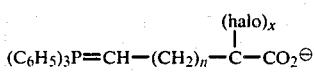

(where A is CH=CH and x is 1 or 2)
to form compounds of the invention IK

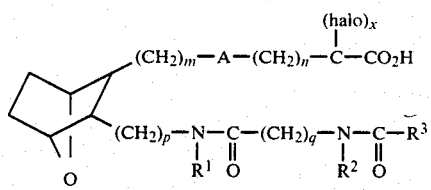

As seen in reaction sequence "K" compounds of the invention wherein Q is

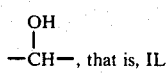

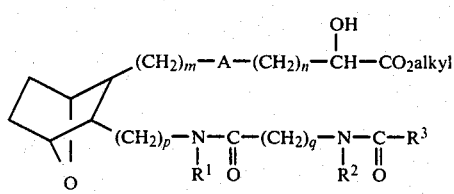

are formed by reacting ester IA to IH with lithium diisopropylamide in the presence of an inert solvent such as tetrahydrofuran at reduced temperatures of lower than about −50° C. and then with oxodiperoxymolybdenum(pyridine)(hexamethylphosphoric triamide) (MoO₅PyHMPA).

In reaction sequence "L", amides of the invention of structure IM

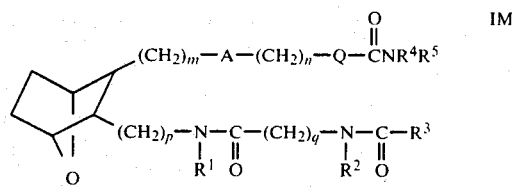

wherein $R^4$ and $R^5$ are independently H, alkyl or aryl are prepared by treating ester IA to IH or IL or esters of IJ or IK with an amine of the structure $HNR^4R^5$  E Compounds of the invention wherein R is tetrazole

and A is CH=CH are prepared as described in reaction sequence "M" wherein alcohol XVII

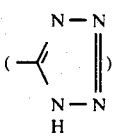

(prepared as described in U.S. Pat. No. 4,143,054) is reacted with a Wittig reagent of the structure G

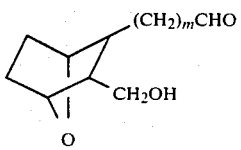

in the presence of a base, such as potassium t-butoxide or sodium hydride-dimethyl sulfoxide employing a molar ratio of XVII:G of within the range of from about 1:1 to about 0.2:1 to form the hydroxymethyl compound IIC

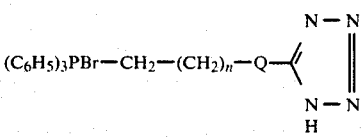

which may then be employed in reaction sequences "A" and "B" in place of compounds II or IIA to form compounds of the invention IN where A is —CH=CH— or IO where A is (CH₂)₂

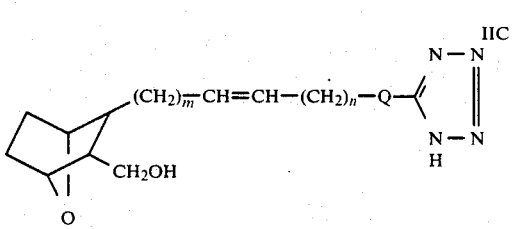

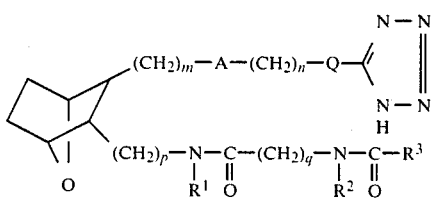

Alternatively, compound IO may be prepared by reducing compound IN by treating with H₂ in the presence of palladium on charcoal.

Compounds of the invention wherein R is tetrazole and Q is CH=CH may also be prepared by reacting aldehyde XX in the reaction sequence "I" with a Wittig reagent of the structure G in the presence of base such as potassium t-butoxide or sodium hydride-dimethyl sulfoxide as described above.

As seen in reaction sequence "O", compounds of the invention wherein R is CH₂OH may be prepared by reducing esters IA to IH, and IL and esters of J and K by treatment with sodium borohydride or lithium borohydride to form compounds of the invention IP

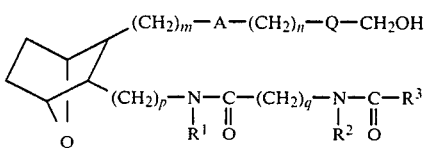

Referring to reaction sequence "P", the esters IA, IA', IB, IB' to IH and IL can be converted to the free acid, that is, to

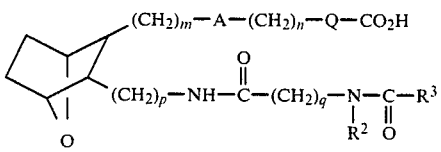

IQ (A is —CH=CH—)
IR (A is (CH₂)₂)
by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention IQ and IR.

In the reaction sequence identified as "Q" where in Formula I, R is

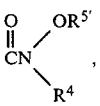

wherein R⁵' is H or alkyl, a solution of acid dissolved in an inert organic solvent such as benzene is treated with oxalyl chloride and a catalytic amount of dimethylformamide (DMF) and the mixture is stirred at room temperature under nitrogen. The resulting acid chloride is dissolved in an inert organic solvent such as tetrahydrofuran and the so-formed solution is added dropwise into a cold solution of amine hydrochloride H

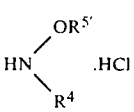

(wherein R⁵' is H or alkyl, employing a molar ratio of acid chloride:H of within the range of from about 0.3:1 to about 1:1 and preferably from about 0.5:1) and triethylamine in aqueous tetrahydrofuran to form the hydroxamate IS.

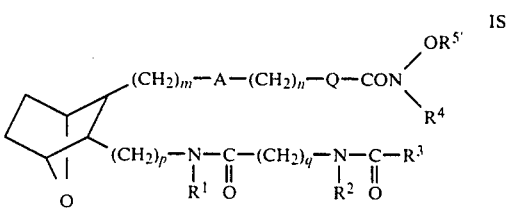

In reaction sequence "R" compounds of the invention wherein R³ is NH₂, that is IT

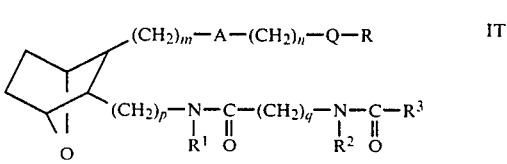

may be prepared by reacting amine VI, VIA or XII with hydantoic acid in the presence of carbonyldiimidazole and then hydrolyzing the resulting product to form IT.

The tris(hydroxmethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

To form the sulfinyl and/or sulfonyl analogs of compounds of formula I wherein R³ is —S—alkyl, —S—aryl, —S—alkylaryl, —alkyl—S—aryl, alkyl—S—alkyl, or —alkyl—S—alkylaryl, such formula I compounds are subjected to oxidation, for example, by reacting same with sodium periodate or potassium monopersulfate (oxone) in the presence of methanol to form the sulfinyl derivative and/or sulfonyl derivative. Mixtures thereof may be separated by chromatography or other conventional separation procedures.

The starting acid VII

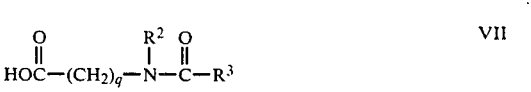

may be prepared by reacting the amino acid J

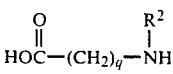

or its acid chloride with acid chloride K

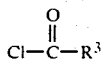
K (or its acid if the acid chloride of J is employed) in the presence of a strong base such as NaOH and water.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

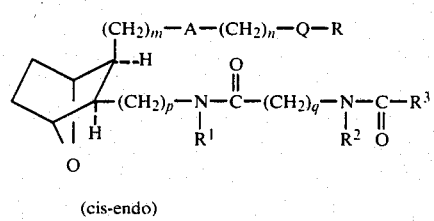

(cis-endo)

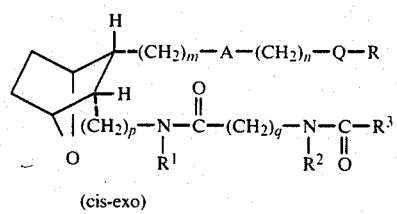

(cis-exo)

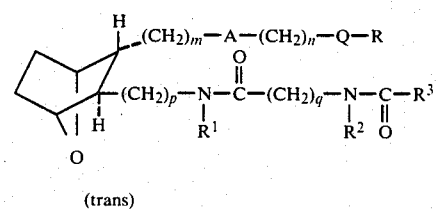

(trans)

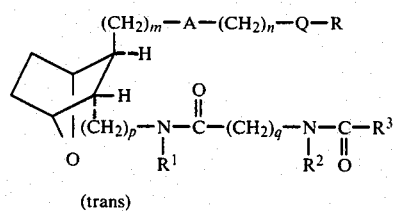

(trans)

The nucleus in each of the compounds of the invention is depicted as

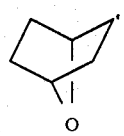

for matter of convenience; it will also be appreciated that the nucleus in the compounds of the invention may be depicted as

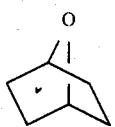

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussed above, certain members additionally serve as intermediates for other members of the group.

The compounds of the invention may also be administered topically to treat peripheral vascular diseases and as such may be formulated as a cream or ointment.

The following examples represent preferred embodiments of the present invention. Unless otherwise indicated, all temperatures are expressed in degrees Centigrade.

EXAMPLE 1

[1S-[1β,2α(5Z),3α,4β]]-7-[3-[[[[(1-Oxohexyl-)amino]acetyl]amino]methyl]-7-oxabicyclo[2.2.1]hept-2-yl]-5-heptenoic acid, methyl ester

A. N-Hexanoylglycine

Glycine (7.5 g, 100 mmol) was dissolved in NaOH solution (NaOH:8 g, $H_2O$:50 ml) and cooled to 0° C. $Et_2O$ (50 ml) was added and n-hexanoyl chloride (13.4 g, 100 mmol) was then added dropwise over 60 minutes at 0° C. under vigorous stirring. The reaction was allowed to warm to room temperature and was stirred for 1 hour. 1N-NaOH (10 ml) was added and the layers were separated. The water layer was washed with $Et_2O$ (20 ml×2). The combined $Et_2O$ layers were extracted with 1N-NaOH (20 ml). The combined water layers were acidified with concentrated HCl to pH 2 and the products were extracted with $Et_2O$ (100 ml×3). The combined $Et_2O$ layers were washed with brine (50 ml)

and dried over MgSO$_4$. Filtration and evaporation of solvent gave a colorless solid (16.2 g), which was crystallized from EtOAc (60 ml) to give colorless needle crystals (10.9 g, 63 mmol, 63%), m.p. 93°–96°.

TLC: silica gel, MeOH, CH$_2$Cl$_2$, HCOOH; 10, 89.5, 0.5, PMA R$_f$=0.45.

B.
[1S-[1β,2α(5Z),3α,4β]]-7-[3-(Tosyloxymethyl)-7-oxabicyclo[2.2.1]hept-2-yl]-5-heptenoic acid, methyl ester Tosyl chloride (4.256 g, 22.4 mmol) dissolved in CH$_2$Cl$_2$ (30 ml) was added dropwise to a magnetically stirred solution of [1S-[1β,2α(5Z),3α,4β]]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/H$_2$O and stirred for 30 minutes. The products were extracted with EtOAc (80 ml×3). The combined EtOAc layers were washed with 3N-HCl (40 ml×3), saturated NaHCO$_3$, brine and dried over MgSO$_4$. Filtration and evaporation of solvent gave a white solid, which was crystallized from isopropyl ether to give the corresponding title tosylate in the form of needle crystals (4.23 g, 89%), m.p. 68°–70° C.

C.
[1S-[1β,2α(5Z),3α,4β]]-7-[(3-(Aminomethyl)-7-oxabicyclo[2.2.1]hept-2-yl]-5-heptenoic acid, methyl ester The title B tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title B tosylate (8.11 g, 19.2 mmol) and purified potassium phthalimide (6.4 g, 34.6 mmol, 1.8 equiv.) in dimethylsulfoxide (70 ml, Burdick & Jackson) were heated at 90°–100° C. for 2½ hours (checked by TLC Et$_2$O-pet ether 2:1, no tosylate remaining). After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3×50 ml), dried (MgSO$_4$), filtered and freed of solvent in vacuo. The remaining solid (7.88 g) was recrystallized from isopropyl ether (~150 ml) to give corresponding phthalimide (6.35 g, 83%) TLC. Et$_2$O-hexane 2:1, UV+vanillin R$_f$=0.38, trace 0.09.

The above phthalimide (5.05 g, 13.8 mmol) was dissolved in distilled CH$_2$Cl$_2$ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more CH$_2$Cl$_2$. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid K$_2$CO$_3$. The amine was extracted into CHCl$_3$ (3×100 ml), dried (MgSO$_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

D.
[1S-[1β,2α(5Z),3α,4β]]-7-[3[[[[(1-Oxohexyl)amino]acetyl]amino]methyl]-7-oxabicyclo[2.2.1]hept-2-yl]-5-heptenoic acid, methyl ester Part A compound (260 mg, 1.5 mmol) was dissolved in distilled THF (12 ml) in an argon atmosphere. After cooling in an ice bath carbonyldiimidazole (CDI) (243 mg, 1.5 mmol) was added. The mixture was stirred cold for 1 hour and then at room temperature for 1 hour. The solution was cooled to 0° C. and a solution of Part C amine (401 mg, 1.5 mmol) in THF (3 ml) was added. The mixture was left stirring overnight at room temperature. The solvent was removed in vacuo and the residue was dissolved in CHCl$_3$ (50 ml). This was washed with 1N HCl (20 ml), 1N NaOH (20 ml) and H$_2$O (20 ml), dried (MgSO$_4$) and freed of solvent in vacuo leaving a viscous oil. The oil was chromatographed on silica gel (30 g, Baker for flash chromatography), eluting with EtOAc and 1% MeOH in EtOAc to give title compound as an oil (425 mg, 67%). TLC: silica gel, 10% MeOH in CH$_2$Cl$_2$, vanillin R$_f$=0.48.

EXAMPLE 2

[1S-[1β,2α(5Z),3α,4β]]-7-[3-[[[[(1-Oxohexyl)amino]acetyl]amino]methyl]-7-oxabicyclo[2.2.1]hept-2-yl]-5-heptenoic acid The Example 1 methyl ester (420 mg, 0.994 mmol) was dissolved in distilled THF (40 ml) and water (8 ml) in an argon atmosphere. 1N LiOH solution (9.5 ml) was added and the mixture was stirred at room temperature for 3¾ hours. After neutralization with 1N HCl (9.5 ml), solid KCl was added and the layers were separated. The aqueous layer was reextracted with CHCl$_3$ (3×50 ml). The combined organic layers (THF+CHCl$_3$) were washed with saturated NaCl solution (2×25 ml), dried (MgSO$_4$), and freed of solvent in vacuo leaving a very viscous oil. This was chromatographed on silica gel (30 g, Baker for flash chromatography) eluting with 4% MeOH in CH$_2$Cl$_2$ to give material which crystallized, (358 mg, 88%). This was recrystallized from acetonitrile (~10 ml) to give title acid, 248 mg, 61%, m.p. 119°–121° C.).

TLC: silica gel, 10% MeOH in CH$_2$Cl$_2$, vanillin, R$_f$=0.37.

Anal Calcd for C$_{22}$H$_{36}$O$_5$H$_2$: C, 64.68; H, 8.88; N, 6.86. Found: C, 64.67; H, 8.87; N, 6.86.

EXAMPLE 3

[1S-[1β,2α(5Z),3α,4β]]-7-[3-[[[[(Butylamino)carbonyl]amino]acetyl]amino]methyl]-7-oxabicyclo[2.2.1]hept-2-yl]-5-heptenoic acid, methyl ester

A. N-[(Butylamino)carbonyl]glycine, ethyl ester

Glycine ethyl ester.HCl (5.58 g, 40 mmol) was suspended in distilled $CH_2Cl_2$ (20 ml). After cooling in an ice bath, distilled $Et_3N$ (6.13 ml, 44 mmol) was added. Distilled n-butyl isocyanate (4.95 ml, 44 mmol) was added. The cooling bath was removed and the mixture was left stirring overnight at room temperature. Additional $Et_3N$ (3.05 ml) was added and the mixture was stirred 3 more hours. After diluting with more $CH_2Cl_2$, the solution was washed with water (50 ml), 1N HCl (50 ml), saturated $NaHCO_3$ solution (50 ml) and water (50 ml). After drying ($MgSO_4$), the solvent was removed in vacuo leaving the title compound (7.641 g, 94%) which slowly crystallized. This was used without further purification.

B. N-[(Butylamino)carbonyl]glycine

Part A ethyl ester (3.378 g, 16.7 mmol) was dissolved in distilled THF (100 ml) and treated with 1N LiOH solution (40 ml). After stirring overnight at room temperature and acidifying with concentrated HCl, solid KCl was added. The layers were separated. The aqueous layer was reextracted with EtOAc (3×50 ml). The combined organic layers (THF and EtOAc) were washed with saturated NaCl solution (25 ml), dried ($MgSO_4$), and freed of solvent in vacuo leaving the title compound, as a white solid (2.81 g, 97%).

C. [1S-[1β,2α(5Z),3α,4β]]-7-[3-[[[[(Butylamino)carbonyl]amino]acetyl]amino]methyl]-7-oxabicyclo[2.2.1]hept-2-yl]-5-heptenoic acid, methyl ester Part B compound (174.2 mg, 1 mmol) was partially dissolved in distilled THF (8 ml) in an argon atmosphere. After cooling in an ice bath, carbonyl diimidazole (CDI) (162 mg, 1 mmol) was added. The mixture was stirred cold 1 hour and at room temperature 1½ hours (became a clear solution near the end of this time). The solution was cooled in an ice bath and a solution of chiral amine prepared in Example 1 Part C (267 mg, 1 mmol) in THF (3 ml) was added. The cooling bath was removed and the mixture was left stirring overnight at room temperature. The solvent was removed in vacuo. $CHCl_3$ (35 ml) was added to the residue. The solution was washed with 1N HCl (15 ml), 1N NaOH (15 ml) and $H_2O$ (15 ml), dried ($MgSO_4$) and freed of solvent in vacuo leaving a very viscous oil (340 mg). This was chromatographed on silica gel (20 g, Baker for flash chromatography), eluting with EtOAc and 5% MeOH in EtOAc to give the title compound as a viscous oil (212 mg, 50%).

TLC: silica gel, 5% MeOH in EtOAc, vanillin, $R_f=0.23$.

EXAMPLE 4

[1S-[1β,2α(5Z),3α,4β]]-7-[3-[[[[(Butylamino)carbonyl]amino]acetyl]amino]methyl]-7-oxabicyclo[2.2.1]hept-2-yl]-5-heptenoic acid Example 3 methyl ester (208 mg, 0.491 mmol) was dissolved in distilled THF (20 ml) and water (4.8 ml) in an argon atmosphere. 1N LiOH solution (4.9 ml) was added and the mixture was stirred at room temperature 5 hours. The mixture was neutralized with 1N HCl solution (4.9 ml) and solid KCl was added. The layers were separated. The aqueous layer was reextracted with $CHCl_3$ (3×25 ml). The combined organic layers (THF and $CHCl_3$) were washed with saturated NaCl solution (15 ml), dried ($MgSO_4$) and freed of solvent in vacuo leaving an oil. This was chromatographed on silica gel (18 g), eluting with 4% MeOH in $CH_2Cl_2$ to give the title compound (158 mg, 78.2%) as a white foam.

TLC: silica gel, 10% MeOH in $CH_2Cl_2$, vanillin, $R_f=0.28$.

Anal Calcd for $C_{21}H_{35}$ $O_5N_3.0.1H_2O$: C, 61.32; H, 8.63; N, 10.21. Found: C, 61.15; H, 8.74; N, 10.23.

EXAMPLE 5

[1S-[1β,2α(5Z),3α,4β]]-7-[3-[[[[Methyl(1-oxohexyl)amino]acetyl]amino]methyl]-7-oxabicyclo[2.2.1]hept-2-yl]-5-heptenoic acid, methyl ester

A. N-Hexanoyl-N-methylglycine

Sarcosine (1.78 g, 20 mmol) was dissolved in 1N NaOH solution (40 ml) and $Et_2O$ (40 ml) was added. After cooling in an ice bath a solution of hexanoyl chloride (3.1 ml, 22 mmol) in $Et_2O$ (10 ml) was added dropwise. The mixture was stirred cold for 1 hour. The pH was then adjusted to about 8 by adding 1N NaOH solution (about 3 ml) and the mixture was stirred at room temperaturee 45 minutes. NaOH solution was added to about pH 9–10. The layers were separated and the aqueous layer was washed with $Et_2O$ (50 ml). After acidification of the aqueous layer with concentrated HCl and saturation with solid KCl, the product was extracted into $CHCl_3$ (3×70 ml). The combined $CHCl_3$ extracts were washed with saturated NaCl solution (25 ml), dried ($MgSO_4$), and freed of solvent leaving the title compound as an oil (3.78 g, quant.) which was used without further purification.

B. [1S-[1β,2α(5Z),3α,4β]]-7-[3-[[[[Methyl(1-oxohexyl)amino]acetyl]amino]methyl]-7-oxabicyclo[2.2.1]hept-2-yl]-5-heptenoic acid, methyl ester Part A compound (187 mg, 1 mmol) was dissolved in distilled THF (8 ml) in an argon atmosphere and cooled in an ice bath. Carbonyldiimidazole (CDI) (162 mg, 1 mmol) was added and the mixture was stirred cold for 1 hour and then for 1 hour at room temperature. After cooling in an ice bath, a solution of chiral amine prepared in Example 1 part C (267 mg, 1 mmol) in THF (3 ml) was added. The ice bath was removed and the mixture was stirred overnight at room temperature. The solvent was removed in vacuo. $CHCl_3$ (35 ml) was added to the residue. The solution was washed with 1N HCl (15 ml), 1N NaOH solution (15 ml) and $H_2O$ (15 ml), dried ($MgSO_4$) and freed of solvent in vacuo leaving an oil (424 mg). This was chromatographed on silica gel (20 g, Baker for flash chromatography), eluting with EtOAc and 2% MeOH in EtOAc to give the title compound as an oil (252 mg, 57.7%).

TLC: silica gel, 5% MeOH in EtOAc, vanillin; $R_f=0.46$.

EXAMPLE 6

[1S-[1β,2α(5Z),3α,4β]]-7-[3-[[[[Methyl(1-oxohexyl)amino]acetyl]amino]methyl]-7-oxabicyclo[2.2.1]hept-2-yl]-5-heptenoic acid The Example 5 methyl ester (248 mg, 0.568 mmol) was dissolved in distilled THF (25 ml) and water (5 ml) in an argon atmosphere. 1N LiOH solution was added and the mixture was stirred at room temperature 4 hours. After neutralizing with 1N HCl solution (5.6 ml) and addition of solid KCl, the layers were separated. The aqueous layer was extracted with $CHCl_3$ (3×25 ml). The combined organic layers (THF+$CHCl_3$) were washed with saturated NaCl solution (15 ml), dried ($MgSO_4$) and freed of solvent in vacuo leaving an oil (242 mg). This was chromatographed on silica gel (20 g, Baker for flash chromatography) eluting with 4% MeOH in $CH_2Cl_2$ to give the title compound (191.8 mg, 79.9%) as a viscous oil.

TLC: silica gel, 10% MeOH in $CH_2Cl_2$, vanillin, $R_f$=0.46.

Anal Calcd for $C_{23}H_{38}O_5N_2$: C, 65.37; H, 9.06; N, 6.63. Found: C, 65.50; H, 9.10; N, 6.74.

EXAMPLE 7

[1S-[1β,2α(5Z),3α,4β]]-7-[3-[[[[(Butoxycarbonyl)amino]acetyl]amino]methyl]-7-oxabicyclo[2.2.1]hept-2-yl]-5-heptenoic acid, methyl ester

A. N-(Butoxycarbonyl)glycine ethyl ester

Glycine ethyl ester.HCl (3.5 g, 25 mmol) was suspended in distilled $CH_2Cl_2$ (25 ml) in an argon atmosphere. After cooling to −40° C. distilled $Et_3N$ (7.65 ml, 55 mmol) was added followed by dropwise addition of a solution of distilled n-butyl chloroformate (3.2 ml, ~25 mmol) in $CH_2Cl_2$ (10 ml). After stirring at −40° for 1 hour the mixture was left in a freezer (−5° C.) overnight. The mixture was stirred at −5° to −10° for 1 hour. More $CH_2Cl_2$ was added followed by water (50 ml). The layers were separated. The organic layer was washed with 1N HCl (50 ml), saturated $NaHCO_3$ solution (50 ml) and water (50 ml), dried ($MgSO_4$), and freed of solvent in vacuo leaving 3.129 g of material. This was combined with material from a 5 mmol run and chromatographed on silica gel (100 g, Baker for flash chromatography), eluting with ether-hexane 1:1 to give the title compound as an oil (3.196 g, 52.5%).

TLC: silica gel, $Et_2O$-hexane 1:1, PMA, $R_f$=0.34.

B. N-(Butoxycarbonyl)glycine

The ethyl ester prepared in part A (3.141 g, 15.47 mmol) was dissolved in 100 ml distilled THF and treated with 1N LiOH solution (40 ml). The mixture was left stirring overnight at room temperature. After acidification with concentrated HCl and addition of solid KCl, the layers were separated. The aqueous layer was reextracted with EtOAc (3×50 ml). The combined organic layers (THF+EtOAc) were washed with saturated NaCl solution (25 ml), dried ($MgSO_4$) and freed of solvent in vacuo leaving the title compound (2.78 g, quant.) which slowly crystallized.

C.

[1S-[1β,2α(5Z),3α,4β]]-7-[3-[[[[(Butoxycarbonyl)amino]acetyl]amino]methyl]-7-oxabicyclo[2.2.1]hept-2-yl]-5-heptenoic acid, methyl ester The acid prepared in part B (175.2 mg, 1 mmol) was dissolved in distilled THF (8 ml) in an argon atmosphere. After cooling in an ice bath carbonyldiimidazole (CDI) (162 mg, 1 mmol) was added. The mixture was stirred cold 1 hour and at room temperature 1 hour. The mixture was again cooled in an ice bath and a solution of chiral amine (prepared in Example I part C, 267 mg, 1 mmol) in THF (3 ml) was added. The cooling bath was removed and the mixture was left stirring overnight at room temperature. The solvent was removed in vacuo. $CHCl_3$ (35 ml) was added. The solution was washed with 1N HCl (15 ml), 1N NaOH (15 ml) and $H_2O$ (15 ml), dried ($MgSO_4$) and freed of solvent in vacuo. The remaining oil (433 mg) was chromatographed on silica gel (20 g of Baker for flash chromatography) eluting with EtOAc to give partially purified material (291 mg). This was rechromatographed on silica gel (20 g), eluting with $Et_2O$ and 2% MeOH in $Et_2O$ to give the title compound (172 mg, 40.5%) as an oil. Additional material (57 mg, 13.4%) was contaminated with a small amount of slower moving material.

TLC: silica gel, 5% MeOH in $Et_2O$, vanillin, $R_f$=0.32.

EXAMPLE 8

[1S-[1β,2α(5Z),3α,4β]]-7-[3-[[[[(Butoxycarbonyl)amino]acetyl]amino]methyl]-7-oxabicyclo[2.2.1]hept-2-yl]-5-heptenoic acid The methyl ester prepared in Example 7 (168 mg, 0.396 mmol) was dissolved in distilled THF (16 ml) and water (3.8 ml) in an argon atmosphere and 1N LiOH solution (3.9 ml) was added. The mixture was stirred at room temperature 5½ hours, then neutralized with 1N HCl solution (3.8 ml). After adding solid KCl the layers were separated. The aqueous layer was reextracted with $CHCl_3$ (3×25 ml). The combined organic layers (THF+$CHCl_3$) were washed with saturated NaCl solution (15 ml), dried ($MgSO_4$) and freed of solvent in vacuo leaving an oil (150 mg). This was chromtographed on silica gel (10 g, Baker for flash chromatography) eluting with 4% MeOH in $CH_2Cl_2$ to give 77 mg of material which appeared clean by TLC: silica gel, 10% MeOH in $CH_2Cl_2$, vanillin, $R_f$=0.43. The material became partially crystalline on standing several days in the cold room. Trituration with $Et_2O$ gave the title compound as a white solid (58.5 mg, 36%) m.p. 104°–106° C.

Anal Calcd for $C_{21}H_{34}O_6N_2$: C, 61.44; H, 8.35; N, 6.82. Found: C, 61.50; H, 8.37; N, 6.98.

EXAMPLE 9

[1S-[1β,2α(5Z),3α,4β]]-2,2-Difluoro-7-[3-[[[[(1-Oxohexyl)amino]acetyl]amino]methyl]-7-oxabicyclo[2.2.1]hept-2-yl]-5-heptenoic acid

A. [1S-[1β,2α,3α,4β]]-2-[3-[[[[(1-Oxohexyl)amino]acetyl]amino]methyl]-7-oxabicyclo[2.2.1]hept-2-yl]acetaldehyde $O_3$ is bubbled through a magnetically stirred solution of [1S-[1β,2α(5Z),3α,4β]]-7-[3-[[[[(1-oxohexyl)amino]acetyl]amino]methyl]-7-oxabicyclo[2.2.1]hept-2-yl]-5-heptenoic acid, methyl ester (211 mg, 0.5 mmol) (prepared as described in Example 1) in $CH_2Cl_2$/MeOH (10 ml/10 ml) at −78° C., until the solution becomes blue. Excess $O_3$ is then purged by a stream of $N_2$ and $(CH_3)_2S$ (1 ml) is added. The reaction is allowed to warm to room temperature and poured into $CH_2Cl_2$ (50 ml), $H_2O$ (10 ml). The products are extracted into $CH_2Cl_2$ layers. The $H_2O$ layer separated is re-extracted with $CH_2Cl_2$ (30 ml). The combined $CH_2Cl_2$ layers are washed with brine (10 ml) and dried over $MgSO_4$. Filtration and evaporation of solvent gives a crude product which is purified by silica gel column chromatography to afford the title compound.

B. (4-Carboxy-4,4-difluorobutyl)triphenylphosphonium bromide (1) Methyl tetrahydrofuroate Methyl furoate (75 g, 0.595 mole) was dissolved in MeOH (150 mll), and poured into a Parr bottle. Air was replaced with argon, and then 10% Pd/C (2.5 g) was added. The atmosphere was replaced with $H_2$ and methyl furoate was hydrogenated at 40 psi for 48 hours. The reaction was filtered through celite pad, and the pad was washed with ether. The filtrate and the wash were combined and distilled to give the title compound (71 g, 0.546 mole, 59° C./5.1 mmHg, 92%) as a colorless liquid.

(2) Methyl 2-acetoxy-5-bromopentanoate

HBr gas was bubbled into $Ac_2O$ (200 ml) at 0° C. for 2 hours. The specific gravity became 1.4. Part (1) methyl tetrahydrofuroate (70 g, 0.538 mole) was added dropwise under maagnetic stirring at 0° C. and the reaction was allowed to warm to room temperature. After stirring overnight, the reaction was poured into ice (~1200 ml) carefully, and left for 30 minutes with occasional swirling. The products were extracted with $Et_2O$ (600 ml×2 and 300 ml). The combined $Et_2O$ layers were washed with dilute NaOH (~0.5%) solution, until the wash became basic. The $Et_2O$ layer was further washed with $H_2O$, dried over $Na_2SO_4$, and filtered. The filtrate was concentrated and distilled to give the title compound (116 g, 0.458 mole, 108° C./1 mmHg, 85%) as a colorless liquid.

(3) Methyl 5-bromo-2-hydroxypentanoate

MeOH (100 ml, distilled over $Mg(OMe)_2$) was saturated with HBr gas at 0° C. This was added to Part (2) compound (60 g, 0.237 mole) in MeOH (200 ml distilled over $Mg(OMe)_2$). The reaction was allowed to warm to room temperature and stirred overnight. The reaction was concentrated in vacuo. Toluene (200 mml) was added to the resulting liquid, and the reaction was concentrated. The same process was repeated twice. The resulting liquid was dissolved in EtOAc (2000 ml) and washed with 0.5% NaOH, brine, and dried over $MgSO_4$. Filtration and evaporation of solvent gave a straw colored oil (44.8 g). This was distilled to give the title compound (34 g, 0.161 mole, 68%) as a colorless liquid.

(4) Methyl 5-bromo-2-oxopentanoate

Jones' reagent ($CrO_3$: 9.58 g, $H_2SO_4$: 8.47 ml, $H_2O$: 36.8 ml) was added to a magnetically stirred solution of Part (3) compound (12.53 g, 59.3 mmole) in acetone (150 ml) at room temperature. The addition was controlled to maintain the temperature below 35° C. After the completion of the addition, the reaction was stirred at room temperature for 45 minutes. Isopropyl alcohol (30 ml) was added dropwise and stirred for 30 minutes. The reaction was then diluted with $H_2O$ (500 ml) and the products were extracted with $CH_2Cl_2$ (1 l.). The $CH_2Cl_2$ layer was washed with brine (100 ml×3) and dried over $MgSO_4$. Filtration and evaporation of solvents gave the title compound (11.4 g, 54.5 mmole, 92%) as a colorless liquid.

(5) Methyl 5-bromo-2,2-difluoropentanoate

Part (4) compound (11.4 g, 54.5 mmole) was added dropwise to $(C_2H_5)_2$ $NSF_3$ (DAST) (6.8 ml, 55.7 mmole) at room temperature. The container of Part (4) was rinsed with $CH_2Cl_2$ (20 ml), which was added to the reaction. The reaction was stirred at room temperature for 1 hour and poured into $H_2O$ (80 ml). The products were extracted with $CH_2Cl_2$ (40 ml×3). The combined $CH_2Cl_2$ layers were washed with $H_2O$ (20 ml×3) and dried over $MgSO_4$. Filtration and evaporation of solvent gave a straw colored liquid (10.8 g). This was distilled to give the title compound (8.4 g, 36.3 mmole, 67%, 41° C./0.015 mmHg) as a colorless liquid.

(6) 5-Bromo-2,2-difluoropentenoic acid

HBr gas was introduced into 48% HBr in $H_2O$ (100 ml) with occasional cooling in an ice bath until the weight became 180 g. The HBr solution was then added to Part (5) compound (8.4 g, 36.3 mmole) at room temperature and the reaction was stirred for 5 hours at room temperature. The reaction was cooled to 0° C. and poured into $Et_2O$ (900 ml) in an ice bath. The products were extracted into the $Et_2O$ layer. The water layer was further extracted with $Et_2O$ (200 ml and 100 ml). The combined ether layers were washed with $H_2O$ (200 ml). The $H_2O$ wash was backwashed with $Et_2O$ (100 ml). The $Et_2O$ layers were combined and dried over $MgSO_4$. Filtration and evaporation of solvent gave the title compound (7.8 g, quant.) as a colorless liquid.

(7) (4-Carboxy-4,4-difluorobutyl)triphenylphosphonium bromide

Acetonitrile (23 ml) was added to a mixture of triphenylphosphine (6.7 g, 25.7 mmole) and Part (6) compound (4.6 g, 21.2 mmole). The solution was heated at gentle reflux under magnetic stirring for 30 hours. Toluene (46 ml) was then added and the reaction was brought to reflux for a brief period. The reaction was allowed to cool to 5° C. and kept overnight. The resulting white precipitates were collected, washed with cold acetonitrile/toluene (½), and dried in a heated vacuum oven (60° C. ~5 mmHg) to give the title bromide (9.8 g, 20.4 mmole, 96.5%) as white solid.

C.
[1S-[1β,2α(5Z),3α,4β]]-2,2-Difluoro-7-[3-[[[[(1-oxohexyl)amino]acetyl]amino]methyl]-7-oxabicyclo[2.2.1-]hept-2-yl]-5-heptenoic acid (4-Carboxy-3,3-difluorobutyl)triphenylphosphonium bromide (1.27 g) (prepared in Part B) is suspended in THF (15 ml). KOt-Amylate (1.7M in toluene, 3 ml) is added at room temperature. The reaction is stirred for 4 hours. The resulting solution is transferred dropwise to aldehyde obtained in Part A, (177.1 mg) in THF (10 ml) at 0° C. The reaction is warmed to room temperature and stirred for 15 hours. Saturated $NH_4Cl$ (25 ml) is added and the products are extracted with EtOAc (40 ml×3). The combined organic layers are washed with brine (30 ml) and dried over $MgSO_4$. Filtration and evaporation of solvents afford a brown colored oil, which is purified by silica gel column to give the title compound.

EXAMPLE 10

[1S-[1β,2α(2E,5Z),3α,4β]]-7-[3-[[[[(1-Oxohexyl)amino]acetyl]amino]methyl]-7-oxabicyclo[2.2.1]hept-2-yl]-2,5-heptadienoic acid (4-Carboxy-3-butenyl)triphenylphosphonium bromide (1.13 g) is suspended in THF (15 ml). KOt Amylate (1.7M in toluene, 3 ml) is added at room temperature. The reaction is stirred for 4 hours. The resulting solution is transferred dropwise to aldehyde obtained in Example 9 Part A, (177.1 mg) in THF (10 ml) at 0° C. The reaction is warmed to room temperature and stirred for 15 hours. Saturated NH4Cl (25 ml) is added and the products are extracted with EtOAc (40 ml×3). The combined organic layers are washed with brine (30 ml) and dried over MgSO4. Filtration and evaporation of solvents afford a crude product, which is purified by silica gel column to give the title compound.

EXAMPLE 11

[1S-[1β,2α(5Z),3α,4β]]-2-Hydroxy-7-[3-[[[[(1-Oxohexyl)amino]acetyl]amino]methyl]-7-oxabicyclo[2.2.1-]hept-2-yl]-5-heptenoic acid, methyl ester Lithium diisopropylamine (LDA) is prepared in an argon atmosphere, by dissolving diisopropylamine (0.89 ml, 644 mg, 6.36 mmol) in THF (30 ml) at 0° C. and adding dropwise a solution of 2N-n-BuLi in hexane (2.55 ml, 5.1 mmol). After stirring at 0° C. for 30 minutes, the LDA solution was cooled at −78° C. Ester prepared in Example 1 (767 mg, 1.8 mmol) dissolved in THF (10 ml) is added to LDA at −78° C. The reaction is stirred at −78° C. for 1 hour. Oxodiperoxymolybdenum(pyridine)(hexamethylphosphoric triamide) (MoOPH) (2.76 g, 6.36 mmol) is added in one portion. The mixture is stirred at −78° C. for 30 minutes and at −30° C. to −40° C. for 1 hour. The reaction is quenched by adding saturated NaHSO3 (20 ml), and allowed to warm to room temperature. After stirring at room temperature for 30 minutes, H2O (0 ml) is added to give two layers which are separated. The aqueous layer is extracted with EtOAc (100 ml×3). The combined organic layers are washed with 1N-HCl (50 ml×2), brine (20 ml×2) and dried over MgSO4. Filtration and evaporation of solvents affords a crude product which is purified by silica gel column to give the title compound.

EXAMPLE 12

[1S-[1β,2α(5Z),3α,4β]]-2-Hydroxy-7-[3-[[[[(1-Oxohexyl)amino]acetyl]amino]methyl]-7-oxabicyclo[2.2.1-]hept-2-yl]-5-heptenoic acid Following the procedure of Example 2 except substituting the Example 11 ester for the Example 1 ester, the title compound is obtained.

EXAMPLE 13

[1S-[1β,2α(5Z),3α,4β]]-7-[3-[[[[(1-Oxohexyl)amino]acetyl]amino]methyl]-7-oxabicyclo[2.2.1]hept-2-yl]-5-heptene-1,2-diol NaBH4 (185 mg) is added to a magnetically stirred solution of hydroxy ester prepared in Example 11 (438 mg) at 0° C. After hydrogen evolution has subsided, the reaction is allowed to warm to room temperature and stirred overnight (16 hours). Saturated NH4Cl (10 ml) is added and stirred for 1 hour. Most of MeOH is removed in vacuo and the residue is partitioned between EtOAc (50 ml) and brine (10 ml). The water layer is reextracted with EtOAc (40 ml×2). The combined organic layers are washed with brine (30 ml) and dried over MgSO4. Filtration and evaporation of solvent give a crude product, which is purified by silica gel column. The title compound is thus obtained.

EXAMPLE 14

[1S-[1β,2α(5Z),3α,4β]]-N-Methyl-7-[3-[[[[(1-Oxohexyl)amino]acetyl]amino]methyl]-7-oxabicyclo[2.2.1]hept-2-yl]-5-heptenamide 40% MeNH2 in H2O (2 ml) is added to a magnetically stirred solution of ester prepared in Example 1 (153 mg) in THF (14 ml) at room temperature. Stirring is continued overnight (17 hours) at room temperature. The reaction is concentrated in vacuo to give a crude product which is purified by silica gel column. The title compound is then obtained.

EXAMPLE 15

[1S-[1β,2α(5Z),3α(R),4β]]-7-[3-[[[1-Oxo-2-[(1-Oxohexyl)amino]propyl]amino]methyl]-7-oxabicyclo[2.2.1-]hept-2-yl]-5-heptenoic acid, methyl ester

A. (2R)-2-(Hexanoylamino)propionic acid

D-alanine (20 mmol) and hexanoyl chloride (22 mmol) were reacted using the method as described in Example 5 Part A to give the title compound as a white crystalline material (2.45 g, 65.5%) after recrystallization from isopropyl ether (20 ml), m.p. 82°–95° C.

B.
[1S-[1β,2α(5Z),3α(R),4β]]-7-[3-[[[1-Oxo-2-[(1-Oxohexyl)amino]propyl]amino]methyl]-7-oxabicyclo[2.2.1-]hept-2-yl]-5-heptenoic acid, methyl ester Part A acid compound (1 mmol) and chiral amine prepared as described in Example 1 Part C (1 mmol) were coupled using CDI (1 mmol) as described in Example 5 Part B. The crude product was chromatographed on silica gel (Baker for flash chromatography) eluting with 2–4% MeOH in Et2O. The eluted product was triturated with Et2O to give the title methyl ester as a whwite solid (217 mg, 50%).

TLC: silica gel, 5% MeOH in Et2O, vanillin $R_f = 0.47$.

EXAMPLE 16

[1S-[1β,2α(5Z),3α(R),4β]]-7-[3-[[[1-Oxo-2-[(1-Oxohexyl)amino]propyl]amino]methyl]-7-oxabicyclo[2.2.1-]hept-2-yl]-5-heptenoic acid The Example 15 methyl ester (215 mg, 0.49 mmol) was hydrolyzed with LiOH solution in a THF-water mixture as described in Example 6. The viscous product was dissolved in EtOAc (~2–3 ml). On standing crystalline material was deposited. This was harvested by filtration and washed with Et2O to give title acid (166.6 mg, 80%), m.p. 101°–103°.

Anal calcd for $C_{23}H_{38}O_5N_2$: C, 65.37; H, 9.06; N, 6.63. Found: C, 65.30; H. 9.16; N, 6.46.

TLC: Silica gel, 10% MeOH in CH2Cl2, vanillin, $R_f = 0.48$.

$[\alpha]_D = +25.5°$ (c=1.37, MeOH).

EXAMPLE 17

[1S-[1β,2α(5Z),3α(S),4β]]-7-[3-[[[1-Oxo-2-[(1-oxohexyl)amino]propyl]amino]methyl]-7-oxabicyclo[2.2.1-]hept-2-yl-]-5-heptenoic acid, methyl ester

A. (2S)-2-(Hexanoylamino)propionic acid

L-Alanine (10 mmol) and hexanoyl chloride (11 mmol) were reacted using the method described in Example 5 Part A to give the title compound as a white crystalline material (1.091 g, 58%) after recrystallization from isopropyl ether (~6 ml).

B.

[1S-[1β,2α(5Z),3α(S),4β]]-7-[3-[[[1-Oxo-2-[(1-oxohexyl)amino]propyl]amino]methyl]-7oxabicyclo[2.2.1-]hept-2-yl]-5-heptenoic acid, methyl ester Part A compound (1 mmol) and chiral amine (prepared as described in Example 1 Part C) (1 mmol) were coupled using CDI (1 mmol) as described in Example 5 Part B. The crude product was chromatographed on silica gel (Baker for flash chromatography) eluting with 2% MeOH in Et$_2$O to give clean title methyl ester (178 mg, 41%) and additional material (129 mg, 29%) contaminated with material moving slower on TLC.

TLC: silica gel, 5% MeOH in Et$_2$O, vanillin, R$_f$=0.55. Slower moving contaminant R$_f$=0.34.

EXAMPLE 18

[1S-[1β,2α(5Z),3α(S),4β]]-7-[3-[[[1-Oxo-2-[(1-oxohexyl)amino]propyl]amino]methyl]-7-oxabicyclo[2.2.1-]hept-2-yl]-5-heptenoic acid The Example 17 methyl ester (175 mg, 0.40 mmol) was hydrolyzed with LiOH in a THF-water mixture as described in Example 6. The viscous product was dissolved in EtOAc (2 ml). Crystalline material was deposited on standing. This was harvested by filtration and washed with cold Et$_2$O to give the title compound (129 mg, 76%), m.p. 104°–106° C.

Anal Calcd for C$_{23}$H$_{38}$O$_5$N$_2$: C, 65.37; H, 9.06; N, 6.63. Found: C, 65.53; H, 9.26; N, 6.50.

TLC: silica gel, 10% MeOH in CH$_2$Cl$_2$, vanillin, R$_f$=0.48.

[α]$_D$= −40°(C=1.29, MeOH)

EXAMPLE 19

[1S-[1β,2α(5Z),3α,4β]]-7-[3-[[[2-Methyl-2[(1-Oxohexyl)amino]-1-oxopropyl]amino]methyl]-7-oxabicyclo[2.2.1]hept-2-yl]-5-heptenoic acid, methyl ester A. 2-(Hexanoylamino)-2-methylpropionic acid 2-Aminoisobutyric acid (2.0 g, 19.4 mmol) and n-hexanoyl chloride (3.0 g, 22.4 mmol) were reacted in the presence of NaOH (1.6 g, 40 mmol) in a mixture of ether and water using the method described in Example 5, Part A. The title compound (1.90 g, 49%) was obtained after crystallization from benzene, m.p. 141°–143° C.

B.

[1S-[1β,2α(5Z),3α,4β]]-7-[3-[[[2-Methyl-2-[(1-Oxohexyl)amino]-1-oxopropyl]amino]methyl]-7-oxabicyclo[2.2.1]hept-2-yl]-5-heptenoic acid, methyl ester Part A compound (1 mmol) was reacted with CDI (1 mmol) and then with chiral amine prepared as described in Example 1 Part C (1 mmol) employing the method described in Example 1 Part D. The crude product was chromatographed on silica gel (25 g, Baker for flash chromatography), eluting with 2% MeOH in Et$_2$O to give title ester (235 mg, 52%) as white crystalline material.

TLC: silica gel, 5% MeOH in Et$_2$O, vanillin, R$_f$=0.46.

EXAMPLE 20

[1-S-[1β,2α(5Z),3α,4β]]-7-[3-[[[2-Methyl-2-[(1-oxohexyl)amino]-1-oxopropyl]amino]methyl]-7-oxabicyclo[2.2.1]hept-2-yl]-5-heptenoic acid The Example 19 methyl ester (231 mg, 0.51 mmol) was hydrolyzed with LiOH in a water-THF mixture as described in Example 6. The product was crystallized from ethyl acetate (~4 ml) to give title acid (154.2 mg, 69%), m.p.81°–87° C.

TLC: silica gel, 10% MeOH in CH$_2$Cl$_2$, vanillin, R$_f$=0.42.

[α]$_D$= −10.1° (c=1.63, MeOH)

Anal calcd for C$_{24}$H$_{40}$O$_5$N$_2$: C, 66.02; H, 9.24; N, 6.42. Found: C, 65.92; H, 9.37; N, 6.46.

EXAMPLE 21

[1S-[1β,2α(5Z),3α,4β]]-7-[3-[[[[(1-Oxoheptyl)amino]acetyl]amino]methyl]-7-oxabicyclo[2.2.1]hept-2-yl]-5-heptenoic acid, methyl ester A. 2-(heptanoylamino)acetic acid Glycine (1.5 g, 20 mmol) and heptanoyl chloride (22 mmol) were reacted in the presence of NaOH (40 mmol) in a mixture of water and ether using the method described in Example 5. The crude product was recrystallized from EtOAc (30 ml) to give title compound (2.71 g, 72%), m.p. 98°–100° C.

B.

[1S-[1β,2α(5Z),3α,4β]]-7-[3-[[[[(1-Oxoheptyl)amino]acetyl]amino]methyl]-7-oxabicyclo[2.2.1]hept-2-yl]-5-heptenoic acid, methyl ester Part A compound (1 mmol) was reacted with CDI (1 mmol) and then with chiral amine (1 mmole) prepared as described in Example 1 Part C employong the method described in Example 5 Part B. The crude product was chromatographed on silica gel (25 g, Baker for flash chromatography) eluting with EtOAc and 2% MeOH in EtOAc to give title ester (270 mg, 62%) as an oil. TLC: silica gel, 5% MeOH in EtOAc, vanillin, R$_f$=0.45.

EXAMPLE 22

[1S-[1β,2α(5Z),3α,4β]]-7-[3-[[[[(1-Oxoheptyl)amino]acetyl]amino]methyl]-7-oxabicyclo[2.2.1]hept-2-yl]-5-heptenoic acid The Example 21 methyl ester (265 mg, 0.607 mmol) was hydrolyzed with LiOH in a water-THF mixture was described in Example 6. The crude crystalline product was recrystalized from EtOAc (4 ml) to give title acid (204 mg, 80%), m.p. 114°–116° C.

TLC:Silica gel, 10% MeOH in CH$_2$Cl$_2$, vanillin, R$_f$=0.40

[α]$_D$= −6.6°(C=1.15, MeOH).

Anal Calcd for C$_{23}$H$_{38}$O$_5$N$_2$: C, 65.37; H, 9.06; N, 6.42. Found: C, 65.38; H, 9.01; N, 6.64.

EXAMPLE 23

[1S-(1β,2α,3α,4β)]-7-[3-[[[[(1-Oxohexyl)amino]acetyl]amino]methyl]-7-oxabicyclo[2.2.1]hept-2-yl]heptanoic acid, methyl ester

A.
[1S-(1β,2α,3α,4β)]-7-[3-(Hydroxymethyl)-7-oxabicyclo[2.2.1]hept-2-yl]heptanoic acid, methyl ester To 800 mg (3.0 mmole) of the [1S-[1β,2α(Z),3α,4β]]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on crabon. The argon atmosphere was exchanged for a slight positive pressure of hydrogen and the reaction was stirred for 8 hours at 25°, filtered through a celite plug and evaporated to provide 730 mg (90%) of the title A compound.

B.
[1S-(1β,2α,3α,4β)]-7-[3-[[[[(1-Oxohexyl)amino]acetyl]amino]methyl]-7-oxabicyclo[2.2.1]hept-2-yl]heptanoic acid, methyl ester Following the procedure of Example 1 except substituting the Part A alcohol-ester for the alcohol ester employing in Example 1 Part B, the title product is obtained.

EXAMPLE 24

[1S-[1β,2α(5Z),3α,4β]]-7-[3-[[[(1-Oxo-3-[(1-oxopentyl)amino]propyl]amino]metyl]-7-oxabicyclo[2.2.1]hept-2-yl]-5-heptenoic acid, methyl ester

A. 3-(Pentanoylamino)propionic acid

β-Alanine (20 mmol) was reacted with valeryl chloride (22 mmol) in the presence of NaOH (40 mmol) in a mixture of H$_2$O and ether using the method described in Example 5. The crude crystalline product (2.75 g, 79%) was recrystallized from a mixture of isopropyl ether (150 ml) and ethyl acetate (10 ml) to give title acid (1.51 g, 44%), m.p. 73°–76° C.

B.
[1S-[1β,2α(5Z),3α,4β]]-7-[3-[[[(1-Oxo-3-[(1-oxopentyl)amino]propyl]amino]methyl]-7-oxabicyclo[2.2.1]hept-2-yl]-5-heptenoic acid, methyl ester Part A acid (1 mmol) was reacted with carbonyl diimidazole (1 mmol) followed by [1S-[1β,2α(5Z),3α,4β]]-7-[3-(aminomethyl)-7-oxabicyclo[2.2.1]hept-2-yl]-5-heptenoic acid, methyl ester (prepared as described in Example 1 Part C (1 mmole)). The crude product was chromatographed on silica gel (25 g, Baker for flash chromatography) eluting with 5–10% MeOH in Et$_2$O to give title product as a white solid (304 mg, 72%).

TLC: silica gel, 10% MeOH in Et$_2$O, vanillin, R$_f$=0.47.

EXAMPLE 25

[1S-[1β,2α(5Z),3α,4β]]-7-[3-[[[1-Oxo-3-[(1-oxopentyl)amino]propyl]amino]methyl]-7-oxabicyclo[2.2.1]hept-2-yl]-5-heptenoic acid The Example 24 methyl ester (301 mg, 0.71 mmol) was hydrolyzed with LiOH in a THF-H$_2$O mixture as described in Example 6 to give a white solid (249 mg). This was recrystallized from EtOAc (~4 ml) to give title acid (218 mg, 75%), m.p. 113°–115°.

TLC: silica gel, 10% MeOH in CH$_2$Cl$_2$, vanillin, R$_f$=0.28

Anal Calcd for C$_{22}$H$_{36}$O$_5$N$_2$: C, 64.68; H, 8.88; N, 6.86. Found: C, 64.65; H, 8.85; N, 6.87.

[α]$_D$=−8.4° (c=1.0, MeOH)

EXAMPLE 26

[1S-[1β,2α(5Z),3α,4β]]-7-[3-[[[[(4-Phenylbenzoyl)amino]acetyl]amino]methyl]-7-oxabicyclo[2.2.1]hept-2-yl]-5-heptenoic acid, methyl ester

A. 2-[(4-Phenylbenzoyl)amino]acetic acid

Glycine (5 mmol) was reacted with 4-biphenylcarbonyl chloride (about 5 mmol) in the presence of 1N NaOH solution (10 ml), ether (21 ml) and THF (2 ml) using the procedure described in Example 5. Most of the product precipitated as a solid on acidification of the aqueous layer during the work up. This was found to be quite insoluble in CHCl$_3$ and EtOAc. It was largely dissolved in CH$_3$CN (~35 ml) and filtered to remove insoluble material. Crystalline acid (0.81 g, 63%) was deposited on cooling, m.p. 207°–218° C. decomp.

B.
[1S-[1β,2α(5Z),3α,4β]]-7-[3-[[[[(4-Phenylbenzoyl)amino]acetyl]amino]methyl]-7-oxabicyclo[2.2.1]hept-2-yl]-5-heptenoic acid, methyl ester Part A acid (1 mmol) was reacted with carbonyldiimidazole (1 mmole) followed by [1S-[1β,2α(5Z),3α,4β]]-7-[3-(aminomethyl)-7-oxabicyclo[2.2.1[hept-2-yl]-5-heptenoic acid, methyl ester (1 mmole) as in Example 1, Part C. After stirring overnight at room temperature, a large amount of solid was still out of solution and TLC indicated the reaction was not complete. DMF (3 ml) was added to give a nearly clear reaction mixture and the mixture was left stirring an additional 24 hours. After the usual work up, the viscous product was chromatographed on silica gel (30 g of Baker for flash chromatography), eluting with 2% MeOH in CH$_2$Cl$_2$. The material obtained from the column was crystallized from ethyl acetate (2 ml) to give title ester (143 mg, 28%) as a white solid.

TLC: silica gel, 10% MeOH in CH$_2$Cl$_2$, UV+vanillin, R$_f$=0.51.

EXAMPLE 27

[1S-[1β,2α(5Z),3α,4β]]-7-[3-[[[[(4-Phenylbenzoyl)amino]acetyl]amino]methyl]-7-oxabicyclo[2.2.1]hept-2-yl]5-heptenoic acid The Example 26 methyl ester (141 mg, 0.279 mmol) was hydrolyzed with LiOH as described in Example 6 to give a white solid. This was triturated with EtOAc to give title acid (118 mg, 86%), m.p. 227°–229° dec.

Anal calcd for C$_{29}$H$_{34}$O$_5$N$_2$: C, 71.00; H, 6.99; N, 5.71. Found: C, 70.90; H, 6.91; N, 5.65.

EXAMPLE 27A

[1S-(1β,2α,3α,4β)]-7-[3-[[[[2-Methyl-2-[(1-oxohexyl)amino]-1-oxopropyl]amino]methyl]-7-oxabicyclo[2.2.1]hept-2-yl]heptanoic acid Following the procedure of Example 1 except substituting the Example 19 Part A acid for the Example 1 Part A acid, the title acid is obtained.

EXAMPLE 28

[1S-[1β,2α(5Z),3α,4β]]-7-[3-[[[[(1-Oxopropyl)amino]acetyl]amino]methyl]-7-oxabicyclo[2.2.1]hept-2-yl]-5-heptenoic acid Following the procedure of Examples 1 and 2 except substituting propanoyl chloride for hexanoyl chloride, the title compound is obtained.

EXAMPLE 28A

[1S-[1β,2α(5Z),3α,4β]]-7-[3-[[[[(1-Oxoethyl)amino]acetyl]amino]methyl]-7-oxabicyclo[2.2.1]hept-2-yl]-5-heptenoic acid Following the procedure of Examples 1 and 2 except substituting acetyl chloride for 6-hexanoyl chloride, the title compound is obtained.

EXAMPLE 29

[1S-[1β,2α(5Z),3α,4β]]-7-[3-[[[[(1-Oxo-2-butenyl)amino]acetyl]amino]methyl]-7-oxabicyclo[2.2.1]hept-2-yl]-5-heptenoic acid Following the procedure of Examples 1 and 2 except substituting 2-butenoyl chloride for hexanoyl chloride, the title compound is obtained.

EXAMPLE 29A

[1S-[1β,2α(5Z),3α,4β]]-7-[3-[[[[(1-Oxo-3-butynyl)amino]acetyl]amino]methyl]-7-oxabicyclo[2.2.1]hept-2yl]-5-heptenoic acid Following the procedure of Examples 1 and 2 except substituting 3-butynoyl chloride for hexanoyl chloride, the title compound is obtained.

EXAMPLE 30

[1S-[1β,2α(5Z),3α,4β]]-7-[3-[[[[(Pentylamino)carbonyl]amino]acetyl]amino]methyl]-7-oxabicyclo[2.2.1]hept-2-yl]-5-heptenoic acid Following the procedure of Examples 3 and 4 except substituting n-pentyl isocyanate for n-butyl isocyanate, the title compound is obtained.

EXAMPLE 30A

[1S-[1β,2α(5Z),3α,4β]]-7-[3-[[[[(Phenylamino)carbonyl]amino]acetyl]amino]methyl]-7-oxabicyclo[2.2.1-]hept-2-yl]-5-heptenoic acid Following the procedure of Examples 3 and 4 except substituting phenyl isocyanate for n-butyl isocyanate, the title compound is obtained.

EXAMPLE 31

[1S-[1β,2α(5Z),3α,4β]]-7-[3[[[[(Phenylcarbonyl)amino]acetyl]amino]methyl]-7-oxabicyclo[2.2.1]hept-2-yl]-5-heptenoic acid Following the procedure of Examples 1 and 2 except substituting benzoyl chloride for hexanoyl chloride, the title compound is obtained.

EXAMPLE 32

[1S-[1β,2α(5Z),3α,4β]]-7-[3-[[[1-Oxo-3-[ethyl(phenylcarbonyl)amino]propyl]amino]methyl]-7-oxabicyclo[2.2.1]hept-2-yl]-5-heptenoic acid Following the procedure of Examples 5 and 6 except substituting 3-(ethylamino)propionic acid for sarcosine and benzoyl chloride for hexanoyl chloride, the title compound is obtained.

EXAMPLE 33

[1S-[1β,2α(5Z),3α,4β]]-7-[3-[[[[(Benzyloxycarbonyl)amino]acetyl]amino]methyl]-7-oxabicyclo[2.2.1]hept-2-yl]-5-heptenoic acid Following the procedure of Examples 7 and 8 except substituting benzyl chloroformate for n-butyl chloroformate, the title compound is obtained.

EXAMPLE 34

[1S-(1β,2α,3α,4β)]-7-[3-[[[[(1-Oxobutyl)amino]acetyl]amino]methyl]-7-oxabicyclo[2.2.1]hept-2-yl]heptanoic acid Following the procedure of Example 23 except substituting butanoyl chloride for hexanoyl chloride, the title compound is obtained.

EXAMPLE 35

[1S-(1β,2α,3α,4β)]-7-[3-[[[[(1-Oxo-2-propenyl)amino]acetyl]amino]methyl]-7-oxabicyclo[2.2.1]hept-2-yl]heptanoic acid Following the procedure of Example 23 except substituting propenyl chloride for hexanoyl chloride, the title compound is obtained.

EXAMPLE 36

[1S-(1β,2α,3α,4β)]-7-[3-[[[[(1-Oxo-4-pentynyl)amino]acetyl]amino]methyl]-7-oxabicyclo[2.2.1]hept-2-yl]heptanoic acid Following the procedure of Example 23 except substituting 4-pentynoyl chloride for hexanoyl chloride, the title compound is obtained.

EXAMPLE 37

[1S-(1β,2α,2α,4β)]-7-[3-[[[[(Phenylamino)carbonyl]amino]acetyl]amino]methyl]-7-oxabicyclo[2.2.1]hept-2-yl]heptanoic acid Following the procedure of Examples 23 and 3 except substituting phenyl isocyanate for n-butyl isocyanate in Example 3 Part A, the title compound is obtained.

EXAMPLE 38

[1S-(1β,2α,3α,4β)]-7-[3-[[[1-Oxo-4-[propyl(1-oxobenzyl)amino]butyl]amino]methyl]-7-oxabicyclo[2.2.1-]hept-2-yl]heptanoic acid Following the procedure of Examples 23 and 5 except substituting 4-(propylamino)butanoic acid for sarcosine in Example 5 Part A, the title compound is obtained.

EXAMPLE 39

[1S-(1α,2α,3α,4β)]-7-[3-[[[[(benzyloxycarbonyl)amino]acetyl]amino]methyl]-7-oxabicyclo[2.2.1]hept-2-yl]heptanoic acid Following the procedure of Examples 23 and 7 except substituting benzyl chloroformate for n-butyl chloroformate, the title compound is obtained.

EXAMPLE 40

[1S-[1β,2α(5Z),3α,4β]]7-[3-[2-[[[(1-Oxohexyl)amino]acetyl]amino]ethyl]-7-oxabicyclo[2.2.1]hept-2-yl]-5-heptenoic acid

A.

[1S-[1β,2α(Z),3α,4β]]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride ((C$_6$H$_5$)$_3$P+—CH$_2$OCH$_3$Cl−) and 235 ml distilled toluene (stored over molecular sieves). The resulting suspension was stirred in an ice-bath, under argon, until cold and than a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1S-[1β,2α(5Z),3α,4β]]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH$_4$Cl, and extracted with ether (4×200 ml). The combined ether phases were washed with NaCl, saturated solution, and dried (MgSO$_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1S-[1β,2α(Z),3α,4β]]-7-[3-(2-oxo)ethyl-7-oxabicyclo[2.2.1]hept-2-yl]-5-heptenoic acid, methyl ester, (B) [1S-[1β,2α(Z),3α,4β]]-7-[3-(2-methoxy)ethenyl-7-oxabicyclo[2.2.1]hept-2-yl]-5-heptenoic acid, methyl ester, and (C) [1S-[1β,2α(Z),3α,4β]]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

[1S-[1α,2α(5Z),3α,4β]]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH$_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO$_3$, saturated NaCl and dried (MgSO$_4$). The ether is evaporated to yield the title B compound.

C.

[1S-[1β,2α(Z),3α,4β]]-7-[3-[2-[[[(1-Oxohexyl)amino]acetyl]amino]ethyl]-7-oxabicyclo[2.2.1]hept-2-yl]-5-heptenoic acid Following the procedure of Examples 1 and 2 except substituting the above part B alcohol for the alcohol used in Example 1 Part B, the title compound is obtained.

EXAMPLE 41

[1S-(1β,2α,3α,4β)]-7-[3-[2-[[[(1-Oxohexyl)amino]acetyl]amino]ethyl]-7-oxabicyclo[2.2.1]hept-2-yl]heptanoic acid Following the procedure of Examples 40 and 1 except substituting [1S-(1β,2α,3α,4β)]-7-[3-formyl-7-oxabicyclo[2.2.1]hept-2-yl]heptanoic acid, methyl ester for [1S-[1β, 2α(Z),3α,4β]]-7-[3-formyl-7-oxabicyclo[2.2.1]hept-2-yl]-5-heptenoic acid, methyl ester, the title compound is obtained.

EXAMPLE 42

[1S-[1β,2α(5Z),3α,4β]]-7-[3-[2-[[[(1-Oxopropyl)amino]acetyl]amino]ethyl]-7-oxabicyclo[2.2.1]hept-2-yl]-5-heptenoic acid Following the procedure of Example 40 except substituting propionoyl chloride for hexanoyl chloride, the title compound is obtained.

EXAMPLE 43

(1β,2α,3α,4β)-7-[3-[2-[[[(1-Oxo-2-butenyl)amino]acetyl]amino]ethyl]-7-oxabicyclo[2.2.1]hept-2-yl]heptanoic acid Following the procedure of Examples 40 and 23 except substituting 2-butenoyl chloride for hexanoyl chloride, the title compound is obtained.

EXAMPLE 44

[1S-[1β,2α(5Z),3α,4β]]-7-[3-[2-[[[[(Phenylamino)carbonyl]amino]acetyl]amino]ethyl]-7-oxabicyclo[2.2.1]hept-2-yl]-5-heptenoic acid Following the procedure of Examples 40 and 3 except substituting phenyl isocyanate for n-butyl isocyanate, the title compound is obtained.

EXAMPLE 45

[1S-[1β,2α(5Z),3α,4β]]-7-[3-[2-[[1-Oxo-3-[ethyl(1-oxophenylmethyl)amino]propyl]amino]ethyl]-7-oxabicyclo[2.2.1]hept-2-yl]-5-heptenoic acid Following the procedure of Examples 40 and 5 except substituting 3-(ethylamino)propionic acid for sarcosine and benzoyl chloride for hexanoyl chloride, the title compound is obtained.

EXAMPLE 46

[1S-[1β,2α(5Z),3α,4β]]-7-[4-[[[(1-Oxohexyl)amino]acetyl]amino]butyl]-7-oxabicyclo[2.2.1]-hept-2-yl]-5-heptenoic acid

A.

[1S-[1β,2α(5Z),3α,4β]]-7-[3-(3-Oxo)propyl-7-oxabicyclo[2.2.1]hept-2-yl-5-heptenoic acid, methyl ester Following the procedure of Example 40 Part A except substituting [1S-[1β,2α(Z),3α,4β]]-7-[3-(2-oxo)ethyl-7-oxabicyclo[2.2.1]hept-2-yl]-5-heptenoic acid, methyl ester for [1S-[1β,2α(Z),3α,4β]]-7-[3-formyl-7-oxabicyclo[2.2.1]hept-2-yl]-5-heptenoic acid, methyl ester, the title A compound is obtained.

B.

[1S-[1β,2α(Z),3α,4β]]-7-[3-(4-Oxo)butyl-7-oxabicyclo[2.2.1]hept-2-yl]-5-heptenoic acid, methyl ester Following the procedure of Example 40 Part A except substituting the aldehyde from Part A above for [1S-[1β,2α(Z),3α,4β]]-7-[3-formyl-7-oxabicyclo[2.2.1-

]hept-2-yl]-5-heptenoic acid, methyl ester, the title B compound is obtained.

C.

[1S-[1β,2α(Z),3α,4β]]-7-[3-(4-Hydroxybutyl)-7-oxabicyclo[2.2.1]hept-2-yl]-5-heptenoic acid, methyl ester Following the procedure of Example 40 Part B except substituting the title B aldehyde for [1S-[1β,2α(Z),3α,4β]]-7-[3-(2-oxo)ethyl-7-oxabicyclo[2.2.1]hept-2-yl]-5-heptenoic acid, methyl ester, the title C alcohol is obtained.

D.

[1S-[1β,2α(Z),3α,4β]]-7-[3-[4-[[[(1-Oxohexyl)amino]acetyl]amino]butyl]-7-oxabicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 47

[1S-[1β,2α(5Z),3α,4β]]-8-[3-[[[[(1-Oxohexyl)amino]acetyl]amino]methyl]-7-oxaabicyclo[2.2.1]-hept-2-yl]-5-octenoic acid

A.

[1S-(1β,2α,3α,4β)]-3-[3-(Hydroxymethyl)-7-oxabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (XIII in reaction sequence C) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO4 and concentrated in vacuo. The solid residue was triturated with hexane (1 liter), filtered, and dried in vacuo to yield 220 g (100%) of desired compound (hemiacetal F in reaction sequence C), m.p. 104°–105° C., [α]$_D$= +27° c = 1 MeOH.

TLC: Silica gel; EtOAc; R$_f$=0.3; Ce(SO4)2.

The above Wittig procedure was repeated on the hemiacetal F used in place of hemiacetal XIII to form the title aldehyde.

B.

[1S-[1β,2α(Z),3α,4β]]-8-[3-(Hydroxymethyl)-7-oxabicyclo[2.2.1]hept-2-yl]-5-octenoic acid, methyl ester A Wittig reagent was prepared in dimethyl sulfoxide (dried over calcium hydride) by adding a solution of sodium methylsulfinylmethide (prepared by heating 600 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of Part A aldehyde 1.02 g (6 mmole) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 70 g of silica gel with 50/50 ethyl acetate-hexane as the eluant which gave 1.1 g of acid. This was treated with diazomethane (CH2N2) in Et2O to give the title compound.

C.

[1S-[1β,2α(Z),3α,4β]]-8-[3-[[[[(1-Oxohexyl)amino]acetyl]amino]methyl]-7-oxabicyclo[2.2.1]hept-2-yl]-5-octenoic acid Following the procedure of Examples 1 and 2 except substituting the title B ester for the ester used in Example 1 Part B, the title compound is obtained.

EXAMPLE 48

[1S-[1β,2α(Z),3α,4β]]-6-[3-[[[[(1-Oxohexyl)amino]acetyl]amino]methyl]-7-oxabicyclo[2.2.1]hept-2-yl]-1-(1H-tetrazol-5-yl)-4-hexene

A.

[1S-[1β,2α(Z),3α,4β]]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S.

Pat. No. 4,143,054) is added in 30 ml of THF. The reaction is stirred for 2 hours and quenched with dilute aqueous HCl. The aqueous layer is extracted with 250 ml ethyl acetate. The combined organic solutions are evaporated in vacuo, diluted with 500 ml of a 5% NaHCO$_3$ solution, washed with 100 ml of ether, acidified with dilute HCl to pH 3, and extracted with three 500 ml portions of ethyl acetate. The combined organic solutions are dried over anhydrous MgSO$_4$, and purified by silica chromatography using a 5% methanol in methylene chloride eluant to provide 2 g of title A compound.

B.
[1S-[1β,2α(5Z),3α,4β]]-6-[3-[[[[(1-Oxohexyl)amino]acetyl]amino]methyl]-7-oxabicyclo[2.2.1]hept-2-yl]-1-(1H-tetrazol-5-yl)-4-hexene Following the procedure of Examples 1 and 2 except substituting the Part A compound for the hydroxymethyl compound used in Example 1 Part B, the title compound is obtained.

EXAMPLE 49

[1S-[1β,2α(5Z),3α,4β]]-7-[3-[[[[(1-Oxohexyl)amino]acetyl]amino]methyl]-7-oxabicyclo[2.2.1]hept-2-yl]-N-hydroxy-N-methyl-5-heptenamide A solution of Example 2 acid (0.82 mmole) in dry benzene (5.0 ml) is treated with oxalyl chloride (1 ml; 11.24 mmole or 13.7 eq.) and a drop of DMF, and stirred at room temperature under nitrogen for 2 hours. The excess oxalyl chloride and solvent are blown off by a stream of nitrogen while heating the reaction flask in a warm water bath and the oil obtained dried in vacuo (oil pump) for 1 hour. The residual acid chloride is dissolved in dry tetrahydrofuran (1.5 ml) and added dropwise into a cold solution (0°, ice-water), of 98% methylhydroxylamine hydrochloride (139.8 mg; 1.64 mmole; 2 eq.) and triethylamine (0.34 ml; 2.46 mmole; 3 eq.) in tetrahydrofuran (2 ml) and water (2.0 ml). The mixture is stirred at 0° under nitrogen for 30 minutes and at room temperature for 5.5 hours, diluted with water (10 ml) and extracted twice with dichloromethane (50 ml). The organic extract is washed with 1N HCl (10 ml), 5% NaHCO$_3$ (5 ml) and water (10 ml), dried (anhydrous MgSO$_4$), filtered and evaporated to dryness giving the crude product, which is purified by silica gel column to afford the title compound.

EXAMPLE 50

[1S-[1β,2α(6Z),3α,4β]]-7-[3-[[[[(1-Oxohexyl)amino]acetyl]amino9 methyl]-7-oxabicyclo[2.2.1]hept-2-yl]-6-heptenoic acid A.
[1S-[1β,2α(6Z),3α,4β]]-7-[3-(Hydroxymethyl)-7-oxabicyclo[2.2.1]hept-2-yl)]-6-heptenoic acid, methyl ester A slurry of carboxypentyl triphenylphosphonium bromide in THF is cooled in an ice bath and treated dropwise with 1.4M KOt-amylate in toluene. After completion of this addition, the reaction mixture is allowed to warm to room temperature and is stirred for 6 hours. To this stirred solution is then added a solution of hemiacetal XIII (reaction sequence G) (prepared as described in Example 3 of U.S. Pat. No. 4,143,054) in THF dropwise over 30 minutes. The reaction mixture is then stirred overnight (15 hours). The mixture is cooled in an ice bath and quenched with HOAc. The solvent is removed in vacuo and the resulting residue is dissolved in saturated NaCl solution. This is extracted with chloroform. The chloroform layers are then extracted with saturated NaHCO$_3$ solution. The aqueous extracts are acidified to pH ~3.5 by addition of aqueous HCl solution, and then are extracted with several portions of chloroform. The combined chloroform extracts are concentrated in vacuo to afford the crude product. The crude acid is esterified with excess ethereal diazomethane at 0° C. and then is purified by chromatography on silica gel to afford the title ester.

B.
[1S-[1β,2α(6Z),3α,4β]]-7-[3-[[[[(1-Oxohexyl)amino]acetyl]amino]methyl]-7-oxabicyclo[2.2.1]hept-2-yl]-6-heptenoic acid Following the procedure of Example 1 except substituting the Part A ester for the hydroxymethyl compound used in Example 1 Part B, the title compound is obtained.

EXAMPLE 51

[1S-[1β,2α(2E),3α,4β]]-7-[3-[[[[(1-Oxohexyl)amino]acetyl]amino]methyl]-7-oxabicyclo[2.2.1]hept-2-yl]-2-heptenoic acid A.
[1S-(1β,2α,3α,4β)]-5-[3-(Hydroxymethyl)-7-oxabicyclo[2.2.1]hept-2-yl]pentanal Following the procedure of Example 47 Part A, except substituting [1S-(1β,2α,3α,4β)]-3-[3-(hydroxymethyl)-7-oxabicyclo[2.2.1]hept-2-yl]propionaldehyde for the hemiacetal XIII (see reaction sequence C or E), [1S-(1β,2α,3α,4β)]-4-[3-(hydroxymethyl)-7-oxabicyclo[2.2.1]hept-2-yl]butanal is obtained. Then by repeating the procedure of Example 47 Part A on [1S-(1β,2α,3α,4β)]-4-[3-(hydroxymethyl)-7-oxabicyclo[2.2.1]hept-2-yl]butanal, the title A aldehyde is produced.

B.
[1S-[1β,2α(2E),3α,4β]]-7-[3-(Hydroxymethyl)-7-oxabicyclo[2.2.1]hept-2-yl]-2-heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title ester.

C.
[1S-[1β,2α(2E),3α,4β]]-7-[3-[[[[(1-Oxohexyl)amino]acetyl]amino]methyl]-7-oxabicyclo[2.2.1]hept-2-yl]-2-heptenoic acid Following the procedure of Example 1 except substituting the Part B ester for the ester used in Example 1 Part B, the title compound is obtained.

EXAMPLE 52

[1S-[1β,2α(5Z),3α,4β]]-7-[3-[(Methylamino)methyl]-7-oxabicyclo[2.2.1]hept-2-yl]-5-heptenoic acid, methyl ester Chiral amine from Example 1, Part C, (1 mmole) and N,N-dimethylformamide dimethylacetal (1.5 mmole) are dissolved in $CH_2Cl_2$ (6 ml). The reaction is stirred at room temperature overnight. The solvent and the excess reagent are evaporated to give crude amidine, which is dissolved in $CH_2Cl_2$ (5 ml). Methyl triflate (2 mmole) is added into the reaction at room temperature and the reaction is stirred for 1 hour at room temperarture. The organic solvent and the excess reagent are evaporated off in vacuo and the residue is treated with methanolic hydrogen chloride at room temperature overnight. The reaction is concentrated in vacuo and the resulting crude product is dissolved in 1N HCl. The water layer is washed with ethyl ether and basified with saturated $NaHCO_3$. The water layer is extracted with ethyl ether, which is dried over $MgSO_4$. Filtration and evaporation of the solvent leave a crude product, which is purified by silica gel column to give the title compound.

The title compound is then employed in place of the chiral amine from Example 1 Part C to prepare compounds of the invention wherein $R^1$ is $CH_3$.

EXAMPLE 53

[1S-[1β,2α(5Z),3α,4β]]-7-[3-[[[[(1-Oxononyl)amino]acetyl]amino]methyl-7-oxabicyclo[2.2.1]hept-2-yl]-5-heptenoic acid, methyl ester

A. N-Nonanoyl glycine

Glycine (20 mmol) was reacted with nonanoyl chloride (22 ml) in the presence of NaOH (40 mmol) in a mixture of water and ether as described in Example 1 Part A. The crude crystalline product (4.25 g) was recrytallized from ethyl acetate (40-50 ml) to give the title compound (3.42 g, 79.5%), m.p. 106°-109° C.

B.

[1S-[1β,2α(5Z),3α,4β]]-7-[3-[[[[(1-Oxononyl)amino]acetyl]amino]methyl]-7-oxabicyclo[2.2.1]hept-2-yl]-5-heptenoic acid, methyl ester Part A compound (1 mmol) was reacted with carbonyldiimidazole (1 mmol) followed by Examle 1 Part C chiral amine as described in Example 1 Part D. The crude product was chromatographed on silica gel (30 g, Baker for flash chromatography) eluting with EtOAc and 2% MeOH in EtOAc to give the title ester (305 mg, 65.6%) as a colorless oil.

TLC: silica gel, 2% MeOH in EtOAc, vanillin, $R_f=0.39$.

EXAMPLE 54

[1S-[1β,2α(5Z),3α,4β]]-7-[3-[[[[(1-Oxononyl)amino]acetyl]amino]methyl]-7-oxabicyclo[2.2.1]hept-2-yl]-5-heptenoic acid The Example 53 methyl ester (302 mg, 6.5 mmol) was hydrolyzed with LiOH in a THF-$H_2O$ mixture as described in Example 2 to give crystalline material. This was recrystallized from EtOAc (about 8 ml) to give title acid (233 mg, 79.5%), m.p. 121°-127° C.

TLC: silica gel, 10% MeOH in $CH_2Cl_2$, vanillin, $R_f=0.44$ $[\alpha]_D = -6.0°$ (c=1, MeOH)

Anal Calcd for $C_{25}H_{42}O_5N_2$: C, 66.64; H, 9.39; N, 6.22. Found: C, 66.27; H, 9.32; N, 6.28.

EXAMPLE 55

[1S-[1β,2α(5Z),3α,4β]]-7-[3-[[[[(1-Oxooctyl)amino]acetyl]amino]methyl]-7-oxabicyclo[2.2.1]hept-2-yl]-5-heptenoic acid, methyl ester

A. N-Octanoylglycine

Glycine (20 mmol) was reacted with octanoyl chloride (22 mmol) in the presence of NaOH (40 mmol) in a mixture of water and ether using the method described in Example 1 Part A. The crude crystalline product (3.06 g, 76%) was recrystallized from EtOAc (15 ml) to give the title compound (1.11 g, 28%), m.p. 105°-107° C.

B.

[1S-[1β,2α(5Z),3α,4β]]-7-[3-[[[[(1-Oxooctyl)amino]acetyl]amino]methyl]-7-oxabicyclo[2.2.1]hept-2-yl]-5-heptenoic acid, methyl ester Part A compound (1 mmol) was reacted with carbonyldiimidazole (1 mmol), followed by Example 1 Part C chiral amine (1 mmol) as described in Example 1 Part D. The crude product was chromatographed on silica gel (30 g, Baker for flash chromatography), eluting with EtOAc and 2% MeOH in EtOAc to give title ester as a colorless oil (330 mg, 73%).

TLC: silica gel, 2% MeOH in EtOAc, vanillin, $R_f=0.26$

EXAMPLE 55A

[1S-[1β,2α(5Z),3α,4β]]-7-[3-[[[[(1-Oxooctyl)amino]acetyl]amino]methyl]-7-oxabicyclo[2.2.1]hept-2-yl]-5-heptenoic acid The Example 55 methyl ester (327 mg, 0.726 mmol) was hydrolyzed with LiOH in a THF-$H_2O$ mixture as described in Example 2 to give a white solid (306 mg). This was crystallized from EtOAc (10 ml) to give title acid (262 mg, 83%), m.p. 129°-131° C.

TLC: silica gel, 10% MeOH in $CH_2Cl_2$, vanillin, $R_f=0.44$.

$[\alpha]_D = -6.0$ (c=0.96, MeOH)

Anal Calcd for $C_{24}H_{40}O_5N_2$: C, 66.02; H, 9.24; N, 6.42. Found: C, 66.02; H. 9.16; N, 6.39.

EXAMPLE 56

[1S-[1β,2α(5Z),3α,4β]]-7-[3-[[[[(1-Oxo-4-phenyl)butyl]amino]acetyl]amino]methyl]-7-oxabicyclo[2.2.1]hept-2-yl]-5-heptenoic acid

A. 4-Phenylbutanoyl glycine ethyl ester

4-Phenylbutyric acid (2.46 g, 15 mmol) was dissolved in distilled THF (70 ml) in an argon atmosphere. After cooling in an ice bath, carbonyldiimidazole (CDI) (2.43 g, 1.5 mmol) was added and the mixture was stirred cold 1 hour and at room temperature 1 hour. The mixture was then cooled and glycine ethyl ester.HCl (2.09 g, 15 mmol) and distilled $Et_3N$ (2.1 ml, 15 mmol) were added. The mixture was left stirring overnight at room temperature. After removal of the solvent in vacuo, $Et_2O$ (200 ml) was added. The solution was washed with 1N HCl (70 ml), 0.5N NaOH (70 ml) and saturated NaCl solution (70 ml), dried ($MgSO_4$) and freed of solvent in vacuo leaving title compound (3.13 g, 84%) as white crystalline material. TLC: silica gel, $Et_2O$, UV; $R_f$ 0.58.

B. 4-Phenylbutanoyl glycine

The Part A ester (3.07 g 12.3 mmol) was hydrolyzed with NaOH (5 g, 125 mmol) in water (60 ml). After stirring at room temperature 6 hours, neutral material was removed by washing with Et$_2$O (2×50 ml). The aqueous solution was then acidified with concentrated HCl solution. The product was extracted into CHCl$_3$ (3×60 ml), dried (MgSO$_4$) and freed of solvent in vacuo leaving a white solid. This was recrystallized from EtOAc (10 ml) to give title compound (2.18 g, 80%), m.p. 99°–101° C.

C. [1S-[1β,2α(5Z),3α,4β]]-7-[3-[[[[(1-Oxo-4-phenyl)butyl]amino]acetyl]amino]methyl]-7-oxabicyclo[2.2.1]hept-2-yl]-5-heptenoic acid, methyl ester Part B acid (1 mmol) was reacted with CDI (1 mmol) and then with Example 1 Part C chiral amine (1 mmol) as described in Example 5 Part B. The crude product was chromatographed on silica gel (26 g, Baker for flash chromatography) eluting with EtOAc and 2% MeOH in EtOAc to give title compound (337 mg, 72%) as an oil.

TLC: silica gel, 2% CH$_3$OH in EtOAc, Ce(SO$_4$)$_2$, R$_f$=0.40.

D. [1S-[1β,2α(5Z),3α,4β]]-7-[3-[[[[(1-Oxo-4-phenyl)butyl]amino]acetyl]amino]methyl]-7-oxabicyclo[2.2.1]hept-2-yl]-5-heptenoic acid The Part C methyl ester (336 mg, 0.71 mmol) was hydrolyzed with LiOH in a water-THF mixture as described in Example 6 The crude crystalline product (300 mg) was recrystallized from a mixture of MeOH and EtOAc to give title compound (247.8 mg, 76%), m.p. 114°–116° C., TLC: silica gel, 2% CH$_3$OH in EtOAc, Ce(SO$_4$)$_2$ R$_f$0.20 [α]$_D$=−5.8 (C=1.7, CH$_3$OH)

Anal calcd for C$_{26}$H$_{36}$N$_2$O$_5$: C, 68.40; H, 7.95; N, 6.14. Found: C, 68.45; H, 8.03; N, 6.11.

EXAMPLE 57

[1S-[1α,2β(Z),3β,4α]]-7-[3-[[[[(Phenylthio)acetyl]amino]acetyl]amino]methyl]-7-oxabicyclo[2.2.1]hept-2-yl]-5-heptenoic acid

A. (Phenylthio)acetyl glycine ethyl ester

The title ethyl ester was prepared from thiophenoxy acetic acid (15 mmol) and the ethyl ester of glycine.HCl using carbonyldiimazole (CDI) as described in Example 56, Part A giving 2.95 g (78%) of solid.

B. (Phenylthio)acetyl glycine

The Part A ethyl ester was hydrolyzed with aqueous NaOH as described in Example 56 Part B to give the title acid (1.041 g, 92%) as a crystalline material.

C. [1S-[1α,2β(Z),3β,4α]]-7-[3-[[[[(Phenylthio)acetyl]amino]acetyl]amino]methyl]-7-oxabicyclo[2.2.1]hept-2-yl]-5-heptenoic acid, methyl ester The Part B acid (1.5 mmol) was reacted with CDI (1.5 mmol) followed by Example 1 Part C chiral amine (1.5 mmol) as described in Example 5 Part B. The crude product was chromatographed on silica gel (30 g, Baker for flash chromatography) eluting the EtOAc and 2% MeOH in EtOAc to give title ester as a solid, 523 mg, 73%.

TLC: silica gel, 5% MeOH in EtOAc, UV+vanillin, R$_f$: 0.48.

D. [1S-[1α,2β(Z),3β,4α]]-7-[3-[[[[(Phenylthio)acetyl]amino]acetyl]amino]methyl]-7-oxabicyclo[2.2.1]hept-2-yl]-5-heptenoic acid The Part C methyl ester (467 mg, 0.98 mmol) was hydrolyzed with 1N LiOH (2 equivalents) as described in Example 6. The crude product was recrystallized from EtOAc (10 ml) to give title acid (419 mg, 93%), m.p. 126°–128° C. [α]$_D$=−5.4° (c=0.8, MeOH).

TLC: silica gel, 10% MeOH in CH$_2$Cl$_2$+HOAc (3 drops/10 ml), UV+vanillin, R$_f$0.51.

Anal Calcd for C$_{24}$H$_{32}$O$_5$N$_2$S: C, 62.58; H, 7.00; N, 6.08; S, 6.96. Found: C, 62.49; H, 7.14; N, 6.02; S, 6.91.

EXAMPLE 58

[1S-[1α,2β(Z),3β,4α]]-7-[3-[[[[3-(4-Hydroxyphenyl)-1-oxopropyl]amino]acetyl]amino]methyl]-7-oxabicyclo[2.2.1]hept-2-yl]-5-heptenoic acid

A. 3-(4-Hydroxyphenyl)propanoyl glycine ethyl ester 3-(4-Hydroxyphenyl)propionic acid (2.49 g, 15 mmol) was reacted with glycine ethyl ester hydrochloride in the presence of CDI and Et$_3$N as described in Example 56 Part A. After removal of the solvent the residue was dissolved in CHCl$_3$ and washed with 1N HCl, saturated NaHCO$_3$ solution and saturated NaCl solution. After drying (MgSO$_4$) and removal of the solvent in vacuo crude title ester remained (2.44 g) as a viscous oil. NMR indicated this contained a major impurity but it was used without further purification.

B. 3-(4-Hydroxyphenyl)propanoyl glycine

Crude Part A ethyl ester was hydrolyzed with NaOH in water as described in Example 56 Part B to give a white solid (1.3 g). This was recrystallized from EtOAc.MeOH to give the title solid (0.98 g, 29% from starting acid).

C. [1S-[1α,2β(Z),3β,4α]]-7-[3-[[[[3-(4-Hydroxyphenyl)-1-oxopropyl]amino]acetyl]amino]methyl]-7-oxabicyclo[2.2.1]hept-2-yl]-5-heptenoic acid, methyl ester Example 1, Part C chiral amine (401 mg, 1.5 mmol) was dissolved in distilled THF (20 ml) in an argon atmosphere. Part B acid (346 mg, 1.55 mmol) was added and the mixture was cooled in an ice bath. Dicyclohexylcarbodiimide (DCC) (319 mg, 1.55 mmol) was added and the mixture was stirred cold 20 minutes and at room temperature overnight. 1N HCl (4 drops) was added and after stirring 10 minutes the solvent was removed in vacuo. EtOAc (8 ml) was added to the residue. After cooling in an ice bath the solid was removed by filtration and washed with cold EtOAc (~10 ml). The filtrate was freed of solvent in vacuo and the remaining material was chromatographed on silica gel (35 g, Baker for flash chromatography) eluting with EtOAc and 3% MeOH in EtOAc to give title ester (243 mg, 34%) as a viscous material.

TLC: silica gel, 8% MeOH in EtOAc, UV+vanillin, R$_f$=0.45.

D.

[1S-[1α,2β(Z),3β,4α]]-7-[3-[[[[[3-(4-Hydroxyphenyl)-1-oxopropyl]amino]acetyl]amino]methyl]-7-oxabicyclo[2.2.1]hept-2-yl]-5-heptenoic acid The Part C methyl ester (243 mg, 0.51 mmol) was dissolved in distilled THF (20 ml) and water (2 ml) in an argon atmosphere and treated with 1N LiOH solution (3 ml). The reaction appeared complete by TLC in 1 hour and at 2 hours was worked up as described in Example 6. The product (212 mg, 90%) was brittle foam which failed to crystallize. $[\alpha]_D = -5.7°$ (c=0.65, MeOH).

TLC: silica gel, 10% MeOH in $CH_2Cl_2$+HOAc (3 drops/10 ml), UV+vanillin. $R_f=0.32$.

Anal Calcd for $C_{25}H_{34}O_6N_2$: C, 65.48; H. 7.47; N, 6.11. Found: C, 65.34; H, 7.59; N, 6.09.

EXAMPLE 59

[1S-[1α,2β(Z),3β,4α]]-7-[3-[[[[(Phenoxyacetyl)amino]acetyl]amino]methyl]-7-oxabicyclo[2.2.1]hept-2-yl]-5-heptenoic acid

A. Phenoxyacetyl glycine

Glycine (20 mmol) was reacted with distilled phenoxyacetyl chloride (22 mmol) in the presence of NaOH (40 mmol) in a mixture of water and ether as described in Example 5 Part A. The crude product was recrystallized from EtOAc (15 ml) to give title acid (2.38 gm, 57%).

B.

[1S-[1α,2β(Z),3β,4α]]-7-[3-[[[[(Phenoxyacetyl)amino]acetyl]amino]methyl]-7-oxabicyclo[2.2.1]hept-2-yl]-5-heptenoic acid, methyl ester Part A acid (1.5 mmol) was reacted with CDI (1.5 mmol), followed by Example 1 Part C chiral amine (1.5 mmol) as described in Example 5, Part B. The crude product was chromatographed on silica gel (25 g, Baker for flash chromatography) eluting with EtOAc and 2% MeOH in EtOAc to give title ester as a white solid (463 mg, 67%).

TLC: silica gel, 5% MeOH in EtOAc, UV+vanillin, $R_f=0.53$.

C.

[1S-[1α,2β(Z),3β,4α]]-7-[3-[[[[(Phenoxyacetyl)amino]acetyl]amino]methyl]-7-oxabicyclo[2.2.1]hept-2-yl]-5-heptenoic acid The Part B methyl ester (463 mg, 1.01 mmol) was hydrolyzed with 1N LiOH (2 equivalents) in a THF-$H_2O$ mixture as described in Example 6 to give a white solid. This was recrystallized from EtOAc (20 ml) containing a few drops of MeOH to give title acid (380 mg, 84.6%). $[\alpha]_D= -5.9°$ (c=0.68, MeOH).

TLC: Silica gel, 10% MeOH in $CH_2Cl_2$+HOAc (3 drops/10 ml), UV+vanillin, $R_f=0.57$.

Anal Calcd for $C_{24}H_{32}O_6N_2$: C, 64.85; H. 7.26; N, 6.30. Found: C, 64.94; H, 7.34; N, 6.26.

EXAMPLE 60

[1S-[1α,2β(5Z),3β,4α]]-7-[3-[[[[(1-Oxo-3-phenylpropyl)amino]acetyl]amino]methyl]-7-oxabicyclo[2.2.1]hept-2-yl]-5-heptenoic acid

A. 3-Phenylpropanoyl glycine

Glycine (1.5 g, 20 mmol) and hydrocinnamoyl chloride (3.37 g, 22 mmol) were reacted in the presence of NaOH (40 mmol) in a mixture of water and ether using the method described in Example 5 Part A. The crude product was extracted into chloroform, dried ($MgSO_4$) and freed of solvent in vacuo leaving a near white solid (3.53 g, 85%). This was recrystallized from EtOAc (13 ml) to give title compound (2.66 g, 64%) m.p. 112°–114° C.

B.

[1S-[1α,2β(5Z),3β,4α]]-7-[3-[[[[(1-Oxo-3-phenylpropyl)amino]acetyl]amino]methyl]-7-oxabicyclo[2.2.1]hept-2-yl]-5-heptenoic acid, methyl ester Part A acid (1 mmol) was reacted with CDI (1 mmol) and then with Example 1 Part C chiral amine (1 mmol) as described in Example 5 Part B. The crude product was chromatographed on silica gel (25 g, Baker for flash chromatography), eluting with 2% MeOH in EtOAc to give title compound (330 mg, 72%) as an oil. TLC: silica gel, 2% MeOH in EtOAc, vanillin $R_f=0.29$.

C.

[1S-[1α,2β(5Z),3β,4α]]-7-[3-[[[[(1-Oxo-3-phenylpropyl)amino]acetyl]amino]methyl]-7-oxabicyclo[2.2.1]hept-2-yl]-5-heptenoic acid The Part B methyl ester (330 mg, 0.72 mmol) was hydrolyzed with LiOH in a water-THF mixture as described in Example 6. The crude crystalline product was recrystallized from EtOAc (12 ml) to give title compound (264 mg, 82.8%) m.p. 119°–122° C.

TLC: silica gel, 8% MeOH in $CH_2Cl_2$, UV and vanillin, $R_f=0.29$.

$[\alpha]_D= -5.9$ (c=1.1, MeOH).

Anal Calcd for $C_{25}H_{34}O_5N_2$: C, 67.85; H, 7.74; N, 6.33. Found: C, 67.62; H, 7.65; N, 6.22.

EXAMPLE 61

[1S-[1α,2β(5Z),3β,4α]]-7-[3-[[[[(1-Oxo-5-phenylpentyl)amino]acetyl]amino]methyl]-7-oxabicyclo[2.2.1]hept-2-yl]-5-heptenoic acid

A. 5-Phenylpentanoyl glycine ethyl ester

5-Phenylvaleric acid (2.67 g, 15 mmol) in distilled THF was reacted with CDI (15 mmol) followed by glycine ethyl ester.HCl (15 mmol) and $(C_2H_5)_3N$ (15 mmol) as described in Example 56 Part A. The crude material (3.25 g, 82%) was used without purification.

B. 5-Phenylpentanoyl glycine

The Part A ester (12.34 mmol) was hydrolyzed with NaOH in water as described in Example 56 Part B. The crude product was recrystallized from EtOAc (12 ml) to give title compound (2.39 g, 82%), m.p. 93°–96° C.

C.

[1S-[1α,2β(5Z),3β,4α]]-7-[3-[[[[(1-Oxo-5-phenylpentyl)amino]acetyl]amino]methyl]-7-oxabicyclo[2.2.1]hept-2-yl]-5-heptenoic acid, methyl ester Part B compound (1 mmol) was reacted with CDI (1 mmol) and then with Example 1 Part C chiral amine (1 mmol) as described in Example 5 Part B. The crude product was chromatographed on silica gel (25 g, Baker for flash chromatography) eluting with 2% MeOH in EtOAc to give title compound (363 mg, 75%) as an oil.

TLC: silica gel, 2% MeOH in EtOAc, vanillin $R_f=0.33$.

D.

[1S-[1α,2β(5Z),3β,4α]]-7-[3-[[[[(1-Oxa-5-phenylpentyl)amino]acetyl]amino]methyl]-7-oxabicyclo[2.2.1]hept-2-yl]-5-heptenoic acid The Part C methyl ester (362 mg, 0.749 mmol) was hydrolyzed with LiOH in a water-THF mixture as described in Example 6. The crude crystalline product was recrystallized from EtOAc (10 ml) containing a few drops of MeOH to give title compound (278 mg, 79%), m.p. 129°-131° C.

TLC: silica gel, 8% MeOH in $CH_2Cl_2$, vanillin, $R_f=0.31$ $[\alpha]_D = -5.5$ (c=0.9, $CH_3OH$)

Anal Calcd for $C_{27}H_{38}O_5N_2$: C, 68.91; H, 8.14; N, 5.95. Found: C, 68.82; H, 8.02; N, 5.88.

EXAMPLE 62

[1S-[1α,2β(Z),3β,4α]]-7-[3-[[[[(4-Cyclohexyl-1-oxobutyl)amino]acetyl]amino]methyl]-7-oxabicyclo[2.2.1]hept-2-yl]-5-heptenoic acid A. 4-Cyclohexylbutanoic acid 4-Phenylbutanoic acid prepared as described in Example 56, Part A was dissolved in glacial acetic acid (25 ml). Platinum oxide (0.1 g) was added and the solution was hydrogenated in the Paar shaker at up to 55 p.s.i. until hydrogen uptake ceased (6.5 hours). The catalyst was removed by filtration and the acetic acid was removed in vacuo. The product crystallized and was recrystallized from $Et_2O$ (20 ml) to give title compound (1.18 g, 77%), m.p. 85°-88° C.

B.

[1S-[1α,2β(Z),3β,4α]]-7-[3-[[[[(4-Cyclohexyl-1-oxobutyl)amino]acetyl]amino]methyl]-7-oxabicyclo[2.2.1]hept-2-yl]-5-heptenoic acid, methyl ester The Part A acid (341 mg, 1.5 mmol) was dissolved in $CHCl_3$ (10 ml) in an argon atmosphere. The solution was cooled in an ice bath and carbonyldiimidazole (2.43 mg, 1.5 mmol) was added. The mixture was stirred cold 30 minutes and at room temperature 1 hour. The hydrochloride of the chiral amine (prepared as described in Example 1 Part C) (456 mg, 1.5 mmol) was added. The solution was cooled in an ice bath and tri-n-butylamine (0.36 ml, 278 mg, 1.5 mmol) was added and the mixture was left stirring overnight at room temperature. More $CHCl_3$ (40 ml) was added and the solution was washed with 1N HCl (20 ml), saturated $NaHCO_3$ solution (20 ml) and saturated NaCl solution (20 ml). After drying ($MgSO_4$), the solvent was removed in vacuo. The product was purified by chromatography on silica gel (30 g of Baker for flash chromatography) eluting with 1% MeOH in EtOAc to give the title methyl ester (661 mg, 92.5%) as an oil which slowly became crystalline. TLC: silica gel, 2% MeOH in EtOAc, vanillin, $R_f=0.26$.

C.

[1S-[1α,2β(Z),3β,4α]]-7-[3-[[[[(4-Cyclohexyl-1-oxobutyl)amino]acetyl]amino]methyl]-7-oxabicyclo[2.2.1]hept-2-yl]-5-heptenoic acid The Part B methyl ester (661 mg, 1.39 mmol) was hydrolyzed with LiOH as described in Example 6. The crude crystalline product was recrystallized from EtOAc (15 ml) and MeOH (1 ml) to give title acid compound (542 mg, 84%), m.p. 141°-143° C.

$[\alpha]_D = -6.0°$ (C=0.96, MeOH)

TLC: silica gel, 10% MeOH in $CH_2Cl_2$, vanillin, $R_f=0.51$

Anal Calcd for $C_{26}H_{42}O_5N_2$: C, 67.50; H, 9.15; N, 6.06. Found: C, 67.58; H, 9.24; N, 6.05.

EXAMPLE 63

[1S-[1α,2β(Z),3β,4α]]-7-[3-[[[[[1-Oxo-3-(phenylthio)propyl]amino]acetyl]amino]methyl]-7-oxabicyclo[2.2.1]hept-2-yl]-5-heptenoic acid A. 3-(Phenylthio)propanoic acid, methyl ester Thiophenol (440 mg, 4 mmol) and $Et_3N$ (70 μl, 0.5 mmol) were dissolved in $CH_2Cl_2$ (5 ml). Methyl acrylate (412 mg, 4.8 mmol) was added dropwise. The reaction was exothermic. After stirring at room temperature for 30 minutes, the excess methyl acrylate was removed in vacuo. TLC: silica gel, $Et_2O$-hexane 1:2, UV $R_f=0.58$. The crude title ester was used without further purification.

B. 3-(Phenylthio)propanoic acid

The crude Part A methyl ester (~4 mmole) was treated with 10 ml 1N NaOH and THF (5 ml). After stirring at room temperature 3 hours, ether (30 ml) was added. The layers were separated and the ether layer was reextracted with 1N NaOH solution (10 ml). The combined aqueous layers were washed with $Et_2O$ (20 ml) and then acidified with concentrated HCl. The product was extracted with $CHCl_3$ (2×30 ml). The chloroform extracts were washed with saturated NaCl solution (2×20 ml), dried ($MgSO_4$) and freed of solvent in vacuo leaving title acid as a white solid (quant.). This was used without further purification.

C. 3-(Phenylthio)propanoyl glycine ethyl ester

Part B acid (0.740 g, 4.06 mmol) was reacted with carbonyldiimidazole (4.06 mmol) followed by glycine ethyl ester.HCl (4.06 mmol) as described in Example 56 Part A to give the title ester (1.00 g, 92%) as crystalline material.

D. 3-(Phenylthio)propanoyl glycine

The Part C ethyl ester (0.96 g, 3.6 mmol) was hydrolyzed with NaOH solution as described in Example 56 Part B to give a white solid which was triturated with $Et_2O$ to give title acid (0.75 g, 87%).

E.

[1S-[1α,2β(Z),3β,4α]]-7-[3-[[[[[1-Oxo-3-(phenylthio)propyl]amino]acetyl]amino]methyl]-7-oxabicyclo[2.2.1]hept-2-yl]-5-heptenoic acid, methyl ester The Part D acid (359 mg, 1.5 mmol) was reacted with carbonyldiimidazole (1.5 mmol) followed by the hydrochloride of Example 1 Part C chiral amine by the procedure described in Example 62 Part B. The crude product was chromatographed on silica gel (30 g, Baker for flash chromatography), eluting with 1% MeOH in EtOAc to give the title methyl ester (623 mg, 85%) as an oil.

TLC: silica gel, 2% MeOH in EtOAc, UV and vanillin $R_f=0.21$.

F.

[1S-[1α,2β(Z),3β,4α]]-7-[3-[[[[[1-Oxo-3-(phenylthio)propyl]amino]acetyl]amino]methyl]-7-oxabicyclo[2.2.1]hept-2-yl]-5-heptenoic acid The Part E methyl ester (623 mg, 1.285 mmol) was dissolved in THF (25 ml) and $H_2O$ (2.5 ml) in an argon atmosphere and treated with 1N LiOH solution (2.6 ml). The mixture was stirred at room temperature for 5 hours and then worked up as described in Example 6. The crude product was chromatographed on silica gel (20 g, Baker for flash chromatography) eluting with 5% MeOH in $CH_2Cl_2$ to give an oil (436 mg, 71%) which crystallized on standing. This was recrystallized from EtOAc (10 ml) to give title acid (136.5 mg, 22%), m.p. 95°-97° C.

TLC: silica gel, 10% MeOH in $CH_2Cl_2$, $R_f$=0.50. $[\alpha]_D$= −5.3° (c=0.88, MeOH)

Anal Calcd for $C_{25}H_{34}O_5N_2S$: C, 63.27; H, 7.22; Found: C, 63.41; H, 7.28; N, 5.94; S, 6.63.

EXAMPLE 64

[1S-[1α,2β(Z),3β,4α]]-7-[3-[[[[[(Phenylmethyl)thio]acetyl]amino]acetyl]amino]methyl]-7-oxabicyclo[2.2.1]hept-2-yl]-5-heptenoic acid

A. Chloroacetyl glycine

Glycine (1.5 g, 20 mmol) was dissolved in 2N NaOH (25 ml, 50 mmol) and ether (20 ml) was added. Chloroacetyl chloride (2.26 g) dissolved in $Et_2O$ (20 ml) was added dropwise at 0° C. The mixture was stirred at 0° for 30 minutes and at room temperature 1 hour. The layers were separated and the water layer was washed with $Et_2O$ (2×20 ml). The water layer was then acidified to pH 2 with concentrated HCl and the product was extracted into EtOAc (3×50 ml). The combined EtOAc extracts were washed with brine, dried ($MgSO_4$), and freed of solvent in vacuo to give title acid compound as a solid (2.56 g, 84%) which was used without further purification.

B. (Benzylthio)acetyl glycine

Part A acid (1.28 g, 8.4 mmol) was dissolved in methanol (10 ml) and cooled in an ice bath. Sodium methoxide (1.08 g, 20 mmol) was added followed by dropwise addition of benzyl mercaptan (1.25 g, 10.08 mmoles). After stirring overnight at room temperature, 1N NaOH solution (10 ml) was added. Ether washes (2×40 ml) removed neutral material. The aqueous layer was then acidified to pH 2 with concentrated HCl. The product was extracted with $Et_2O$ (3×50 ml), washed with brine, dried ($MgSO_4$) and freed of solvent in vacuo leaving a white solid. This was recrystallized from benzene to give title acid compound (1.28 g, 64%).

C.

[1S-[1α,2β(Z),3β,4α]]-7-[3-[[[[[(Phenylmethyl)thio]acetyl]amino]acetyl]amino]methyl]-7-oxabicyclo[2.2.1]hept-2-yl]-5-heptenoic acid, methyl ester Part B acid (359 mg, 1.5 mmol) was reacted with carbonyldiimidazole (1.5 mmol) followed by Example 1 Part C chiral amine.HCl 3 (1.5 mmol) using the procedure described in Example 62. The crude product was chromatographed on silica gel (30 g, Baker for flash chromatography) eluting with 1% MeOH in EtOAc to give title ester as an oil (625 mg, 85%).

TLC: silica gel 2% MeOH in EtOAc, UV+vanillin, $R_f$=0.30.

D.

[1S-[α,2β(Z),3β,4α]]-7-[3-[[[[[(Phenylmethyl)thio]acetyl]amino]acetyl]amino]methyl]-7-oxabicyclo[2.2.1]hept-2-yl]-5-heptenoic acid The Part C methyl ester (625 mg, 1.28 mmol) was hydrolyzed with 1N LiOH solution (2.6 ml) in a THF-water mixture as described in Example 5 Part B. The reaction mixture was worked up at 5 hours 20 minutes. The crude product was recrystallized from EtOAc (15 ml) to give title product (427 mg, 77.7%), m.p. 98°-101° C. $[\alpha]_D$= −5.7° (c=0.95, MeOH)

TLC: silica gel, 10% MeOH in $CH_2Cl_2$, UV+vanillin, $R_f$=0.4.

Anal Calcd for $C_{25}H_{34}O_5N_2S$: C, 63.27; H, 7.22; N, 5.90; S, 6.76. Found: C, 63.53; H, 7.42; N, 5.91; S, 6.77.

EXAMPLE 65

[1S-[1α,2β(Z),3β,4α]]-7-[3-[[[[[(Butylthio)acetyl]amino]acetyl]amino]methyl]-7-oxabicyclo[2.2.1]hept-2-yl]-5-heptenoic acid

A. (Butanethio)acetyl glycine

Example 64 Part A acid compound (1.28 g, 8.4 mmol) was reacted with 1-butanethiol using the procedure described in Example 64. The crude product was crystallized with diisopropylether (∼10 ml) to give title acid (0.55 g, 32%).

B.

[1S-[1α,2β(Z),3β,4α]]-7-[3-[[[[[(Butylthio)acetyl]amino]acetyl]amino]methyl]-7-oxabicyclo[2.2.1]hept-2-yl]-5-heptenoic acid, methyl ester Part A acid (308 mg, 1.5 mmol) was reacted with carbonyldiimidazole (1.5 mmol) followed by Example 1 Part C chiral amine hydrochloride (1.5 mmol) using the procedure described in Example 62. The crude product was chromatographed on silica gel (30 g, Baker for flash chromatography) eluting with 1% MeOH in EtOAc to give title compound (538 mg, 79%) as an oil.

TLC: silica gel, 2% MeOH in EtOAc, UV+vanillin, $R_f$=0.29.

C.

[1S-[1α,2β(Z),3β,4α]]-7-[3-[[[[[(Butylthio)acetyl]amino]acetyl]amino]methyl]-7-oxabicyclo[2.2.1]hept-2-yl]-5-heptenoic acid The Part B methyl ester (538 mg, 1.18 mmol) was hydrolyzed with 1N LiOH solution (2.4 ml) in a tetrahydrofuran-water mixture using the procedure described in Example 5 Part B. The reaction mixture was worked up in 5 hours. The crude product was crystallized from EtOAC (20 ml) to give title product (444 mg, 85.4%), m.p. 114°-116°.

$[\alpha]_D$= −6.0° (c=0.9, MeOH)

TLC: silica gel, 10% MeOH in $CH_2Cl_2$, UV+vanillin, $R_f$=0.3.

Anal calcd for $C_{22}H_{36}O_5N_2S$: C, 59.97; H, 8.24; N, 6.36; S, 7.28. Found: C, 59.77; H, 8.31; N, 6.30; S, 7.27.

EXAMPLE 66

[1S-[1α,2β(Z),3β,4α]]-7-3-[[[[[(Cyclohexylmethyl)thio]acetyl]amino]acetyl]amino]methyl]-7-oxabicyclo[2.2.1]hept-2-yl]-5-heptenoic acid

A. Cyclohexylmethylthiol acetate

Cyclohexylmethyl mesylate (1.92 g, 10 mol) and $KSCOCH_3$ (1.25 g) were suspended in distilled tetrahydrofuran (THF). The reaction mixture was heated under reflux for 3 hours. Additional $KSCOCH_3$ (1.25 g) and THF (9 ml) were added and the mixture was heated under reflux an additional 3 hours. $Et_2O$ (100 ml) was added and the mixture was washed with brine (30 ml). The aqueous layer was reextracted with $Et_2O$ (30 ml). The combined organic layers were washed with brine (15 ml), dried (MgSO$_4$) and freed of solvent to give a straw colored oil (1.8 g). This was chromatographed on silica gel (50 g, Baker for flash chromatography) eluting with 2% Et$_2$O in hexane to give title compound (1.189 g, 69%) as an oil.

TLC: silica gel, 10% Et$_2$O in hexane, UV and I$_2$, R$_f$=0.48.

B. [(Cyclohexylmethyl)thio]acetyl glycine

Part A compound (6 mmol) and the Example 64 Part A acid (6 mmol) were reacted in the presence of NaOMe (17 mmol) as described in Example 64 Part B. The crude product was crystallized from diisopropyl ether to give title compound (516 mg, 35%).

C.
[1S-[1α,2β(Z),3β,4α]]-7-[3-[[[[[(Cyclohexylmethyl)thio]acetyl]amino]acetyl]amino]methyl]-7-oxabicyclo[2.2.1]hept-2-yl]-5-heptenoic acid, methyl ester Part B compound (368 mg, 1.5 mmol) was coupled with Example 1 Part C chiral amine.HCl (456 mg, 1.5 mmol) in the presence of carbonyl diimidazole (CDI) (1.5 mmol) as described in Example 62 Part B. The crude product was chromatographed on silica gel (30 g, Baker for flash chromatography) eluting with 1% MeOH in EtOAc to give title compound (542 mg, 73%) as an oil.

TLC: silica gel, 2% MeOH in EtOAc, UV+vanillin, R$_f$=0.38.

D.
[1S-[1α,2β(Z),3β,4α]]-7-[3-[[[[[(Cyclohexylmethyl)thio]acetyl]amino]acetyl]amino]methyl]-7-oxabicyclo[2.2.1]hept-2-yl]-5-heptenoic acid The Part C methyl ester (542 mg, 1.09 mmol) was hydrolyzed with 1N LiOH (4 ml) in a mixture of THF and water as described in Example 6. The crude product was recrystallized from EtOAc (30 ml) to give title acid (439 mg, 83%), m.p. 131°–133° C.

TLC: silica gel, 10% MeOH in CH$_2$Cl$_2$, UV+vanillin, R$_f$=0.56. [α]$_D$=−5.0° (c=0.95, MeOH).

Anal Calcd for C$_{25}$H$_{40}$N$_2$O$_5$S: C, 62.47; H, 8.39; N, 5.83; S, 6.67. Found: C, 62.37; H, 8.46; N, 5.77; S, 6.60.

EXAMPLE 67

[1S-[1α,2β(Z),3β,4α]]-7-3-[[[[(Phenylsulfinyl)acetyl]amino]acetyl]amino]methyl]-7-oxabicyclo[2.2.1]hept-2-yl]-5-heptenoic acid Powdered NaIO$_4$ (385 mg, 1.8 mmol) was dissolved in water (12 ml). A solution of Example 57 acid compound (276 mg, 0.6 mmol) in methanol (20 ml) was added. The mixture was stirred overnight at room temperature. Most of the methanol was removed in vacuo. Saturated NaCl solution (50 ml) was added. The product was extracted with CHCl$_3$ (3×50 ml). The combined chloroform extracts were washed with NaCl solution (20 ml), dried (MgSO$_4$), and freed of solvent in vacuo leaving an oil. This was chromatographed on silica gel (4 g, Baker for flash chromatography) eluting with 5% MeOH in CH$_2$Cl$_2$ to give a foam (254 mg) which gave very broad peaks in $^1$H NMR. The material was dissolved in CHCl$_3$ (100 ml) and washed with 1N HCl solution (2×25 ml) and saturated NaCl solution (2×20 ml), dried (MgSO$_4$) and freed of solvent in vacuo leaving title acid (213 mg, 74%) as a white solid foam.

TLC: silica gel, 10% MeOH in CH$_2$Cl$_2$, UV+vanillin, R$_f$=0.14.

Anal calcd for C$_{24}$H$_{32}$N$_2$O$_6$S.0.2H$_2$O: C, 60.02; H, 6.80; N, 5.83; S, 6.68. Found: C, 59.95; H, 6.83; N, 5.78; S, 6.53.

[α]$_D$=−9.7° (c=0.7, MeOH)

EXAMPLE 68

[1S-[1α,2β(Z),3β,4α]]-7-[3-[[[[[(Phenylsulfonyl)acetyl]amino]acetyl]amino]methyl]-7-oxabicyclo[2.2.1]hept-2-yl]-5-heptenoic acid Example 67 acid compound (44.5 mg, 0.9 mmol) was dissolved in methanol (10 ml) and cooled in an ice bath. Oxone (810 mg~2.7 mmol) dissolved in water (10 ml) was added. The mixture was stirred at room temperature 4 hours, then diluted with water (30 ml). The product was extracted into CHCl$_3$ (3×35 ml). The combined CHCl$_3$ extracts were washed with saturated NaCl solution (2×20 ml), dried (MgSO$_4$), and freed of solvent in vacuo leaving an oil (430 mg). This was chromatographed on silica gel (10 g, Baker for flash chromatography) eluting with 5% MeOH in CH$_2$Cl$_2$ to give title acid, 165 mg (37%).

TLC: silica gel, 10% MeOH/CH$_2$Cl$_2$, UV+vanillin. R$_f$=0.27.

Anal Calcd for C$_{24}$H$_{32}$O$_7$N$_2$S.0.5H$_2$O: C, 57.46; H, 6.63; N, 5.59. Found: C, 57.27; H, 6.44; N, 5.55.

EXAMPLES 69 TO 104

Following the procedures outlined in the specification and described in the above working Examples, the following compounds may be prepared.

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 69. | 2 | CH=CH | $\begin{array}{c}CH_3\\-CH-\end{array}$ | CH=CH | $\begin{array}{c}O\\\parallel\\CN-OCH_3\\\mid\\H\end{array}$ | 3 | $C_2H_5$ | $(CH_2)_7$ | $C_3H_7$ | $\begin{array}{cc}H & H\\ \mid & \mid \\ -CH_2-C=C-CH_3\end{array}$ |
| 70. | 3 | $(CH_2)_2$ | $\begin{array}{c}CH_3\\-C-\\CH_3\end{array}$ | $CH_2$ | $\begin{array}{c}O\\\parallel\\CN-OC_2H_5\\\mid\\CH_3\end{array}$ | 4 | H | $\begin{array}{c}CH_3\\-CH-\end{array}$ | $C_4H_9$ | $OC_6H_5$ |
| 71. | 4 | $(CH_2)_2$ | $(CH_2)_4$ | $\begin{array}{c}OH\\\mid\\-CH-\end{array}$ | $\begin{array}{c}O\\\parallel\\CNHC_6H_5\end{array}$ | 1 | $C_3H_7$ | $-CH_2-$ | $C_5H_{11}$ | $C_6H_5$ |
| 72. | 1 | CH=CH | $\begin{array}{c}CH_3\ CH_3\\-C-CH_2-\end{array}$ | $\begin{array}{c}F\\\mid\\-CH-\end{array}$ | $CO_2Li$ | 2 | H | $\begin{array}{c}CH_3\\\mid\\CH_3-CH\\-CH_2-\end{array}$ | H | $CH_2C_6H_5$ |
| 73. | 0 | CH=CH | $\begin{array}{c}CH_3\ CH_3\\-CH-CH-\end{array}$ | $\begin{array}{c}F\ F\\-C-\\\end{array}$ | $CO_2N_a$ | 3 | $CH_3$ | $\begin{array}{c}CH_3\ CH_3\\-C-\\CH_2-\end{array}$ | H | $-(CH_2)_2C_6H_5$ |
| 74. | 1 | $(CH_2)_2$ | $\begin{array}{c}CH_3\\-C-CH_2-\\F\end{array}$ | CH=CH | $CO_2$ glucamine salt | 4 | $C_2H_5$ | $\begin{array}{c}CH_3\\-CH_2-CH-CH_2-\end{array}$ | H | $-C_6H_4-p-CH_3$ |
| 75. | 2 | CH=CH | $\begin{array}{c}F\ F\\-CH-CH-\end{array}$ | $CH_2$ | $CO_2$ tris salt | 1 | H | $-(CH_2)_3-$ | $CH_3$ | $-C_6H_4-p-OH$ |
| 76. | 3 | $(CH_2)_2$ | $\begin{array}{c}F\\-C-CH_2-\end{array}$ | $\begin{array}{c}OH\\\mid\\-CH-\end{array}$ | $CH_2OH$ | 2 | $C_4H_9$ | $\begin{array}{c}C_2H_5\\-CH_2-CH-\end{array}$ | $CH_3$ | $-OCH_2C_6H_5$ |
| 77. | 4 | $(CH_2)_2$ | $-(CH_2)_5$ | $\begin{array}{c}F\\\mid\\-CH-\end{array}$ | $\begin{array}{c}N=N\\\diagup\ \ \diagdown\\\ \ \ \ \ \ N-H\end{array}$ | 3 | H | $\begin{array}{c}CH_3\\-CH_2-C-CH_2-\\H\end{array}$ | $CH_3$ | $-SC_2H_5$ |

-continued $$\underset{O}{\overset{(CH_2)_m-A-(CH_2)_n-Q-R}{\diagup}}\quad (CH_2)_p-\underset{R^1}{\overset{}{N}}-\underset{O}{\overset{}{C}}-(CH_2)_q-\underset{R^2}{\overset{}{N}}-\underset{O}{\overset{}{C}}-R^3$$

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 78. | 0 | CH=CH | $\underset{-CH_2-CH-CH_2-}{\overset{CH_3}{\mid}}$ | $\underset{-C-}{\overset{F\ \ F}{\diagup\diagdown}}$ | $\underset{CNH_2}{\overset{O}{\parallel}}$ | 4 | $CH_2$ | $\underset{-C-CH_2-}{\overset{CH_3}{\underset{CH_3}{\mid}}}$ | $C_2H_5$ | $-OC_6H_5$ |
| 79. | 0 | $(CH_2)_2$ | $\underset{-CH_2C-}{\overset{CH_3\ \ CH_3}{\diagup\diagdown}}$ | — | $\underset{CNOH}{\overset{O}{\underset{H}{\parallel}}}$ | 1 | $C_2H_5$ | $(CH_2)_2$ | $CH_3$ | $-NH_2$ |
| 80. | 1 | CH=CH | $CH_2$ | — | $\underset{CN(CH_3)_2}{\overset{O}{\parallel}}$ | 2 | $C_2H_5$ | $-CH_2-$ | H | $-NHCH_3$ |
| 81. | 2 | $(CH_2)_2$ | $(CH_2)_2$ | $CH_2$ | $\underset{CN-CH_3}{\overset{O}{\underset{OH}{\parallel}}}$ | 3 | $CH_3$ | $\underset{-CH_2-C-CH_2-}{\overset{CH_3}{\underset{CH_3}{\mid}}}$ | $C_4H_9$ | $-NHC_6H_5$ |
| 82. | 3 | CH=CH | $(CH_2)_3$ | — | $CO_2H$ | 4 | $C_2H_5$ | $-CH_2-CH-CH-CH_2-$ $CH_3\ CH_3$ | $CH_3$ | $NCH_3(C_2H_5)$ |
| 83. | 4 | $(CH_2)_2$ | $(CH_2)_4$ | CH=CH | $CH_2OH$ | 1 | $C_3H_7$ | $(CH_2)_2$ | $C_2H_5$ | $-N(CH_3)_2$ |
| 84. | 0 | CH=CH | $\underset{-CH_2C-}{\overset{F\ \ F}{\diagup\diagdown}}$ | $CH_2$ | $\underset{}{\overset{N\diagdown\ \ \diagup N}{\underset{N}{\diagup\diagdown}H}}$ (methyl) | 2 | $C_4H_9$ | $(CH_2)_3$ | $CH_3$ | H |
| 85. | 1 | $(CH_2)_2$ | $\underset{-CH_2C-}{\overset{CH_3\ \ CH_3}{\diagup\diagdown}}$ | $\underset{-CH-}{\overset{OH}{\mid}}$ | $\underset{CN(C_2H_5)_2}{\overset{O}{\parallel}}$ | 3 | $C_5H_{11}$ | $\underset{-CH-CH_2-}{\overset{F}{\mid}}$ | $C_3H_7$ | $-NH-CH_2-C_6H_5$ |
| 86. | 2 | CH=CH | $(CH_2)_5$ | $\underset{-CH-}{\overset{F}{\mid}}$ | $\underset{CNHC_6H_5}{\overset{O}{\parallel}}$ | 4 | H | $\underset{-C-CH_2}{\overset{F}{\underset{F}{\mid}}}$ | $C_4H_9$ | $-(CH_2)_2CH=CHCH_3$ |

-continued $$\text{[bicyclic structure]}-(CH_2)_m-A-(CH_2)_n-Q-R$$

$$(CH_2)_p-\underset{R^1}{N}-\underset{\parallel}{C}-(CH_2)_q-\underset{R^2}{N}-\underset{\parallel}{C}-R^3$$
$$\phantom{(CH_2)_p-N-}O\phantom{-(CH_2)_q-N-}O$$

| Ex. No. | m | A | $(CH_2)_n$ | Q | R | p | $R^1$ | $(CH_2)_q$ | $R^2$ | $R^3$ |
|---|---|---|---|---|---|---|---|---|---|---|
| 87. | 3 | $(CH_2)_2$ | $\underset{\|}{CH_3}\underset{\|}{\overset{F}{\|}}$ $-CH-CH-$ | $\underset{F}{\overset{F}{\diagdown}}C\diagup$ | $CH_2OH$ | 1 | H | $(CH_2)_2$ | H | $C_6H_5$ |
| 88. | 4 | $(CH_2)_2$ | $(CH_2)_2$ | CH=CH | $\underset{H}{\overset{N=N}{\diagup\diagdown}}\underset{}{\overset{}{\diagdown}}\underset{CH_3}{\overset{N-N}{\diagup}}$ | 2 | H | $CH_2$ | H | $-CH_2C_6H_5$ |
| 89. | 0 | CH=CH | $(CH_2)_3$ | $\underset{\|}{\overset{OH}{\|}}$ $-CH-$ | $CO_2CH_3$ | 3 | $CH_3$ | $(CH_2)_3$ | $C_3H_7$ | $-SC_4H_9$ |
| 90. | 2 | $(CH_2)_2$ | $(CH_2)_4$ | $CH_2$ | $CO_2CH_3$ | 4 | $CH_3$ | $(CH_2)_8$ | H | $-SC_6H_5$ |
| 91. | 3 | CH=CH | $(CH_2)_5$ | — | $CO_2H$ | 1 | $CH_3$ | $(CH_2)_{10}$ | H | $-NCH_3(C_6H_5)$ |
| 92. | 2 | CH=CH | $CH_2$ | CH=CH | $CO_2H$ | 1 | H | $(CH_2)_2$ | $CH_3$ | H |
| 93. | 3 | $(CH_2)_2$ | $(CH_2)_2$ | $CH_2$ | $CH_2OH$ | 2 | $C_2H_5$ | $(CH_2)_3$ | H | $CH_3$ |
| 94. | 4 | CH=CH | $(CH_2)_3$ | $\underset{\|}{\overset{OH}{\|}}$ $-CH-$ | $\underset{H}{\overset{N=N}{\diagup\diagdown}}\underset{}{\overset{}{\diagdown}}\underset{CH_3}{\overset{N-N}{\diagup}}$ | 3 | H | $(CH_2)_4$ | H | $-CH=CH-CH_3$ |
| 95. | 1 | $(CH_2)_2$ | $(CH_2)_4$ | $\underset{F}{\overset{F}{\diagdown}}C\diagup$ | $\underset{\|}{\overset{O}{\|}}$ $CN(CH_3)C_2H_5$ | 1 | $CH_3$ | $(CH_2)_5$ | $CH_3$ | $-C\equiv C-CH_3$ |
| 96. | 0 | CH=CH | $(CH_2)_5$ | $\underset{F}{\overset{F}{\diagdown}}C\diagup$ | $\underset{\|}{\overset{O}{\|}}$ $CN-OH$ $\underset{}{\overset{\|}{CH_3}}$ | 2 | H | $(CH_2)_6$ | $C_2H_5$ | $-CH_2-C\equiv C-CH_3$ |
| 97. | 1 | CH=CH | $(CH_2)_3$ | — | $CO_2H$ | 1 | H | $CH_2$ | H | $\underset{}{\overset{O}{\|}}$ $-SC_6H_5$ |

-continued

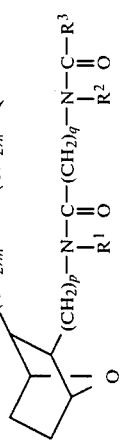

| Ex. No. | m | A | (CH₂)ₙ | Q | R | p | R¹ | (CH₂)q | R² | R³ |
|---|---|---|---|---|---|---|---|---|---|---|
| 98. | 1 | CH=CH | CH₂ | — | CO₂H | 1 | H | CH₂ | | $-\overset{O}{\underset{\underset{O}{\|}}{\overset{\|}{S}}}C_2H_5$ |
| 99. | 2 | (CH₂)₂ | (CH₂)₃ | CH₂ | CH₂OH | 2 | CH₃ | (CH₂)₂ | H | —SCH₂C₆H₅ |
| 100. | 3 | CH=CH | (CH₂)₃ | CH=CH | CO₂H | 3 | H | (CH₂)₃ | | —CH₂—S—C₆H₅ |
| 101. | 4 | (CH₂)₂ | (CH₂)₃ | — | $-\overset{O}{\overset{\|}{C}}NH_2O$ | 1 | CH₅ | CH₂ | CH₃ | —CH₂—S—CH₂—C₆H₅ |
| 102. | 2 | CH=CH | (CH₂)₃ | CH₂ | CO₂H | 2 | H | CH₂ | H | —CH₂—O—CH₂—C₆H₅ |
| 103. | 3 | CH=CH | CH₂ | — | CO₂H | 1 | CH₃ | CH₂ | H | —CH₂—N—CH₂C₆H₅<br>H |
| 104. | 2 | (CH₂)₂ | (CH₂)₃ | CH₂ | CO₂CH₃ | 1 | H | (CH₂)₂ | CH₃ | —CH₂—S—C₄H₉ |

What is claimed is:
1. A compound having the structure

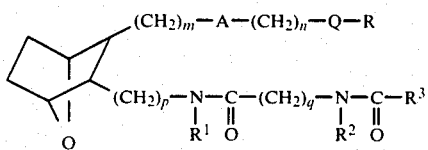

including all stereoisomers thereof, wherein m is 0 to 4; A is —CH=CH— or —CH$_2$—CH$_2$—; n is 1 to 5; Q is —CH=CH—, —CH$_2$—,

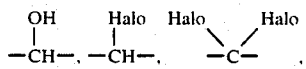

or a single bond; R is CO$_2$H, CO$_2$alkyl, CO$_2$ alkali metal, CO$_2$ polyhydroxyamine salt, —CH$_2$OH,

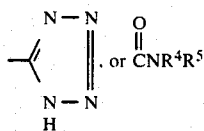

wherein R$^4$ and R$^5$ are the same or different and are H, lower alkyl, hydroxy, lower alkoxy or aryl at least one of R$^4$ and R$^5$ being other than hydroxy and lower alkoxy; p is 1 to 4; R$^1$ is H or lower alkyl; q is 1 to 12; R$^2$ is H or lower alkyl; and R$^3$ is H, lower alkyl, lower alkenyl containing 2 to 12 carbons, lower alkynyl containing 2 to 12 carbons, aryl, arylalkyl, lower alkoxy, arylalkoxy, aryloxy, amino, alkylamino, arylamino, arylalkylamino,

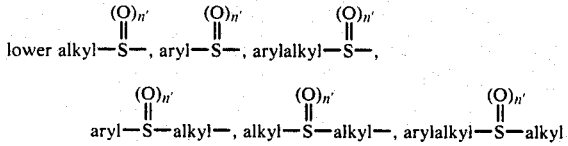

(wherein n' is 0, 1 or 2), alkylaminoalkyl, arylaminoalkyl, arylalkylaminoalkyl, alkoxyalkyl, aryloxyalkyl, or arylalkoxyalkyl;

(CH$_2$)$_m$, (CH$_2$)$_n$ and (CH$_2$)$_p$ may be unsubstituted or substituted with 1 or 2 lower alkyl groups and/or 1 or 2 halogens;

(CH$_2$)$_q$ may be unsubstituted or substituted by 1 or 2 halo, hydroxy, alkoxy, amine, alkylamine, arylamine, amide, thioamide, thiol, alkylthio, arylthio, cyano, or nitro groups;

amide refers to

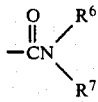

wherein R$^6$ and R$^7$ are independently hydrogen, lower alkyl or aryl;

wherein lower alkyl or alkyl alone or as part of another group contains 1 to 12 carbons and is unsubstituted or is substituted with halo, CF$_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;

aryl alone or as part of another group contains 6 to 10 carbons in the ring portion and is unsubstituted or is substituted with 1 or 2 lower alkyl groups, 1 or 2 halogens, 1 or 2 alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups;

cycloalkyl alone or as part of another group contains 3 to 12 carbons and is unsubstituted or is substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups; and alkanoyl refers to lower alkyl linked to a carbonyl group.

2. The compound as defined in claim 1 wherein R$^3$ is lower alkyl, lower alkoxy or arylthioalkyl.

3. The compound as defined in claim 1 wherein A is CH=CH.

4. The compound as defined in claim 1 wherein m is 1 and n is 1 to 4.

5. The compound as defined in claim 1 wherein p is 1 and q is 1.

6. The compound as defined in claim 1 wherein Q is a single bond or CH$_2$.

7. The compound as defined in claim 1 wherein R is CO$_2$alkyl or CO$_2$H.

8. The compound as defined in claim 1 wherein R$^1$ is H and R$^2$ is H or CH$_3$.

9. The compound as defined in claim 1 wherein m is 1, n is 2 to 4, Q is CH$_2$, a single bond, CH=CH,

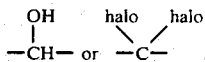

R is CO$_2$alkyl, CO$_2$H, CH$_2$OH, or

p is 1, R$^1$ is H, q is 1, R$^2$ is H or lower alkyl and R$^3$ is lower alkyl, alkoxy or phenylthiomethyl.

10. The compound as defined in claim 1 having the name [1S-[1β,2α(5Z),3α,4β]]-7-[3-[[[[(1-oxohexyl)amino]acetyl]amino]methyl]-7-oxabicyclo[2.2.1]hept-2-yl]-5-heptenoic acid or esters thereof, including all stereoisomers thereof.

11. The compound as defined in claim 1 having the name [1S-[1β,2α(5Z),3α,4β]]-7-[3-[[[[[(butylamino)carbonyl]amino]acetyl]amino]methyl]-7-oxabicyclo[2.2.1-]hept-2-yl]-5-heptenoic acid or esters thereof, including all stereoisomers thereof.

12. The compound as defined in claim 1 having the name [1S-[1β,2α(5Z),3α,4β]]-7-[3-[[[[methyl(1-oxohexyl)amino]acetyl]amino]methyl]-7-oxabicyclo[2.2.1-]hept-2-yl]-5-heptenoic acid or esters thereof, including all stereoisomers thereof.

13. The compound as defined in claim 1 having the name [1S-[1β,2α(5Z),3α,4β]]-7-[3-[[[[(butoxycarbonyl- )amino]acetyl]amino]methyl]-7-oxabicyclo[2.2.1]hept-2-yl]-5-heptenoic acid or esters thereof, including all stereoisomers thereof.

14. The compound as defined in claim 1 having the name [1S-[1β,2α(5Z),3α(R),4β]]-7-[3-[[[1-Oxo-2-[(1-oxohexyl)amino]propyl]amino]methyl]-7-oxabicyclo[2.2.1]hept-2-yl]-5-heptenoic acid or esters thereof, including all stereoisomers thereof.

15. The compound as defined in claim 1 having the name [1S-[1β,2α(5Z),3α(S),4β]]-7-[3-[[[1-Oxo-2-[(1-oxohexyl)amino]propyl]amino]methyl]-7-oxabicyclo[2.2.1]hept-2-yl]-5-heptenoic acid or esters thereof, including all stereoisomers thereof.

16. The compound as defined in claim 1 having the name [1S-[1β,2α(5Z),3α,4β]]-7-[3-[[[(1-oxo-4-phenyl)-butyl]amino]acetyl]amino]methyl]-7-oxabicyclo[2.2.1]hept-2-yl]-5-heptenoic acid or esters thereof including all stereoisomers thereof.

17. The compound as defined in claim 1 having the name [1S-[1α,2β(Z),3β,4α]]-7-[3-[[[[(phenylthio)acetyl]amino]acetyl]amino]methyl]-7-oxabicyclo[2.2.1]hept-2-yl]-5-heptenoic acid or esters thereof including all stereoisomers thereof.

18. The compound as defined in claim 1 having the name [1S-[1α,2β(Z),3β,4α]]-7-[3-[[[[3-(4-hydroxyphenyl)-1-oxopropyl]amino]acetyl]amino]methyl]-7-oxabicyclo[2.2.1]hept-2-yl]-5-heptenoic acid or esters thereof including all stereoisomers thereof.

19. The compound as defined in claim 1 having the name [1S-[1α,2β(Z),3β,4α]]-7-[3-[[[(phenoxyacetyl)amino]acetyl]amino]methyl]-7-oxabicyclo[2.2.1]hept-2-yl]-5-heptenoic acid or esters thereof including all stereoisomers thereof.

20. The compound as defined in claim 1 having the name [1S-[α,2β(5Z),3β,4α]]-7-[3-[[[[(1-oxo-3-phenyl)propyl)amino]acetyl]amino]methyl]-7-oxabicyclo[2.2.1]hept-2-yl]-5-heptenoic acid or esters thereof including all stereoisomers thereof.

21. The compound as defined in claim 1 having the name [1S-[1α,2β(5Z),3β,4α]]-7-[3-[[[(1-oxo-5-phenylpentyl)amino]acetyl]amino]methyl]-7-oxabicyclo[2.2.1]hept-2-yl]-5-heptenoic acid or esters thereof including all stereoisomers thereof.

22. The compound as defined in claim 1 having the name [1S-[1α,2β(Z),3β,4α]]-7-[3-[[[[(4-cyclohexyl-1-oxobutyl)amino]acetyl]amino]methyl]-7-oxabicyclo[2.2.1]hept-2-yl]-5-heptenoic acid or esters thereof including all stereoisomers thereof.

23. The compound as defined in claim 1 having the name [1S-[1α,2β(Z),3β,4α]]-7-[3-[[[[1-oxo-3-(phenylthio)propyl]amino]acetyl]amino]methyl]-7-oxabicyclo[2.2.1]hept-2-yl]-5-heptenoic acid or esters thereof including all stereoisomers thereof.

24. The compound as defined in claim 1 having the name [1S-[1α,2β(Z),3β,4α]]-7-[3-[[[[(phenylmethyl)thio]acetyl]amino]acetyl]amino]methyl]-7-oxabicyclo[2.2.1]hept-2-yl]-5-heptenoic acid or esters thereof including all stereoisomers thereof.

25. The compound as defined in claim 1 having the name [1S-[1α,2β(Z),3β,4α]]-7-[3-[[[[(butylthio)acetyl]amino]acetyl]amino]methyl]-7-oxabicyclo[2.2.1]hept-2-yl]-5-heptenoic acid or esters thereof including all stereoisomers thereof.

26. The compound as defined in claim 1 having the name [1S-[1α,2β(Z),3β,4α]]-7-[3-[[[[(cyclohexylmethyl)thio]acetyl]amino]acetyl]amino]methyl]-7-oxabicyclo[2.2.1]hept-2-yl]-5-heptenoic acid or esters thereof including all stereoisomers thereof.

27. The compound as defined in claim 1 having the name [1S-[1α,2β(Z),3β,4α]]-7-[3-[[[[(Phenylsulfinyl)acetyl]amino]acetyl]amino]methyl]-7-oxabicyclo[2.2.1]hept-2-yl]-5-heptenoic acid or esters thereof including all stereoisomers thereof.

28. The compound as defined in claim 1 having the name [1S-[1α,2β(Z),3β,4α]]-7-[3-[[[[(phenylsulfonyl)acetyl]amino]acetyl]amino]methyl]-7-oxabicyclo[2.2.1]hept-2-yl]-5-heptenoic acid or esters thereof including all stereoisomers thereof.

29. A method of inhibiting platelet aggregation and/or bronchoconstriction, which comprises administering to the circulatory system of a mammalian host an effective amount of a compound as defined in claim 1 or a pharmaceutically acceptable salt thereof.

30. The method as defined in claim 29 wherein said compound is administered in an amount within the range of from about 1 to about 100 mg/kg.

31. A composition for inhibiting platelet aggregation and/or bronchoconstriction comprising an effective amount of a compound as defined in claim 1 or a pharmaceutically acceptable salt thereof, and a pharmaceutically acceptable carrier therefor.

32. A method of treating peripheral vascular diseases, which comprises topically or systemically administering to a mammalian host an effective amount of a compound as defined in claim 1 or a pharmaceutically acceptable salt thereof.

33. The compound as defined in clam 1 having the name [1S-[1β,2α(5Z),3α,4β]]-7-[3-[[[(1-oxoheptyl)amino]acetyl]amino]methyl-7-oxabicyclo[2.2.1]hept-2-yl]-5-heptenoic acid or esters thereof, including all stereoisomers thereof.

* * * * *